(12) United States Patent
Maecker et al.

(10) Patent No.: US 9,895,441 B2
(45) Date of Patent: Feb. 20, 2018

(54) METHODS OF TREATING CANCER USING PD-L1 AXIS BINDING ANTAGONISTS AND VEGF ANTAGONISTS

(71) Applicant: Genentech, Inc., South San Francisco, CA (US)

(72) Inventors: Heather Maecker, Palo Alto, CA (US); Bryan Irving, San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/556,774

(22) Filed: Dec. 1, 2014

(65) Prior Publication Data

US 2015/0320859 A1    Nov. 12, 2015

Related U.S. Application Data

(63) Continuation of application No. PCT/US2013/043452, filed on May 30, 2013.

(60) Provisional application No. 61/653,861, filed on May 31, 2012.

(51) Int. Cl.

| A61K 39/395 | (2006.01) |
| A61K 31/282 | (2006.01) |
| A61K 31/519 | (2006.01) |
| A61K 31/513 | (2006.01) |
| C07K 16/22  | (2006.01) |
| C07K 16/28  | (2006.01) |
| A61K 39/00  | (2006.01) |

(52) U.S. Cl.
CPC ........ *A61K 39/3955* (2013.01); *A61K 31/282* (2013.01); *A61K 31/513* (2013.01); *A61K 31/519* (2013.01); *A61K 39/39558* (2013.01); *C07K 16/22* (2013.01); *C07K 16/2827* (2013.01); *A61K 2039/505* (2013.01); *A61K 2039/507* (2013.01)

(58) Field of Classification Search
None
See application file for complete search history.

(56) References Cited

U.S. PATENT DOCUMENTS

| 6,884,879 | B1 | 4/2005 | Baca et al. |
| 7,060,269 | B1 | 6/2006 | Baca et al. |
| 7,169,901 | B2 | 1/2007 | Baca et al. |
| 7,297,334 | B2 | 11/2007 | Baca et al. |
| 7,365,166 | B2 | 4/2008 | Baca et al. |
| 7,375,193 | B2 | 5/2008 | Baca et al. |
| 8,217,149 | B2 | 7/2012 | Irving et al. |
| 8,314,213 | B2 * | 11/2012 | Bernett ............... C07K 16/00 530/388.2 |
| 2010/0203056 | A1 * | 8/2010 | Irving ................ A61K 31/7068 424/139.1 |
| 2015/0190506 | A1 | 7/2015 | Cheung et al. |
| 2016/0222117 | A1 | 8/2016 | Irving et al. |
| 2016/0257738 | A1 | 9/2016 | Baca et al. |
| 2017/0000885 | A1 | 1/2017 | Pheeetal et al. |
| 2017/0107287 | A1 | 4/2017 | Irving et al. |

FOREIGN PATENT DOCUMENTS

| EP | 2172219 A1 | 4/2010 |
| JP | 2006-340714 A | 12/2006 |
| JP | 2007-525466 A | 9/2007 |
| JP | 2008-544755 A | 12/2008 |
| JP | 2012-500847 A | 1/2012 |
| JP | 2012-503984 A | 2/2012 |
| JP | 2012-511329 A | 5/2012 |
| JP | 2015-500207 A | 5/2015 |
| WO | WO-2005/000900 A1 | 1/2005 |
| WO | 2006/121168 A1 | 11/2006 |
| WO | WO-2006/121169 A1 | 11/2006 |
| WO | 2007/005874 A2 | 1/2007 |
| WO | WO-2010/027423 A2 | 3/2010 |
| WO | 2010/036959 A2 | 4/2010 |
| WO | 2010/077634 A1 | 7/2010 |
| WO | WO-2011/066342 A2 | 6/2011 |
| WO | WO-2013/079174 A1 | 6/2013 |

OTHER PUBLICATIONS

Giantonio et al. (Journal of Clinical Oncology, 2007, 25:1539-1544).*
Almagro & Fransson, Frontiers in Bioscience 2008; 13:1619-33.*
De Genst et al., Developmental and Comparative Immunology, 2006, 30:187-98.*
Choi et al., 2011, Molecular BioSystems, 2011, 7:3327-334.*
Griffiths et al. (The EMBO Journal, 1993, 12:725-734).*
Klimka et al., British Journal of Cancer, 2000, 83:252-260.*
Beiboer et al., Journal of Molecular Biology, 2000, 296:833-849.*
Berglund et al, 2008, Protein Science, 17:606-613.*
Tzartos et al., Methods in Molecular Biology, 1996, 66:55-66.*
Robertson et al. (Clinical Colorectal Cancer, 2009, 8:59-60).*
Blank et al., "Combination of targeted therapy and immunotherapy in melanoma" Cancer Immunol Immunother 60:1359-1371 (2011).
CureTech Ltd., 'Study to Evaluate the Safety, Tolerability and Efficacy of FOLFOX + CT-011 Versus FOLFOX Alone Administered Intravenously to Patients with Colorectal Adenocarcinoma Previously Untreated for Metastatic Disease', Clinicaltrials.gov, Apr. 28, 2009 (Apr. 28, 2009), XP002711443, Retrieved from the Internet: URL:http://clinicaltrials.gov/ct2/show/NCT00890305, in 3 pages.

(Continued)

*Primary Examiner* — Julie Wu

(74) *Attorney, Agent, or Firm* — Morrison & Foerster LLP

(57) ABSTRACT

The present invention describes combination treatment comprising a PD-1 axis binding antagonist, chemotherapy and optionally a VEGF antagonist and methods for use thereof, including methods of treating conditions where enhanced immunogenicity is desired such as increasing tumor immunogenicity for the treatment of cancer.

10 Claims, 4 Drawing Sheets

(56) References Cited

OTHER PUBLICATIONS

Emmanouilides et al., "Front-line Bevacizumab in combination with Oxaliplatin, Leucovorin and 5-Fluorouracil (FOLFOX) in patients with metastatic colorectal cancer: a multicenter phase II study" BMC Cancer 7(91):1-7 (2007).
Flies et al., "Blockade of the B7-H1/PD-1 Pathway for Cancer Immunotherapy" Yale Journal of Biology and Medicine 84:409-421 (2011).
International Search Report issued in International Application No. PCT/US2013/043452, in 9 pages (dated Oct. 30, 2013).
Pal et al., "Novel Therapies for Metastatic Renal Cell Carcinoma: Efforts to Expand beyond the VEGF/mTOR Signaling Paradigm" Mol Cancer Ther 11:526-537 ( 2012).
Topalian et al., "Targeting the PD-1/B7-H1(PD-L1) pathway to activate anti-tumor immunity" Current Opinion in Immunology 24:207-212 (2012).
International Preliminary Report on Patentability issued in International Application No. PCT/US2013/043452, dated Dec. 2, 2014, in 21 pages.
Bensen et al. "The PD-1/PDL1 Axis Modulates the Natural killer Cell Versus Multiple Myeloma Effect: A Therapeutic Target for CT-011, A Novel Monoclonal Anti-PD-1 Antibody," *Blood* 116(13):2286-2294, (Sep. 30, 2010, e-pub. May 11, 2010).
Clinical Trials. "NCT00890305 Study to Evaluate the Safety, Tolerability and Efficacy of FOLFOX + CT-011 Versus FOLFOX Alone," located at <http://clinicaltrails.gov/ct2/showNCT00890305>, last visited on Oct. 24, 2016, 3 pages, (Jun. 2015).
Medivation. (Mar. 9, 2016). "U.S. FDA Lifts Partial Clinical Hold on Medivation'S Pidilizumab. Potentially Pivotal Phase II Trial in DLBCL and Other Studies May Proceed," *Marketwire*, two pages.

\* cited by examiner

METHODS OF TREATING CANCER USING PD-L1 AXIS BINDING ANTAGONISTS AND VEGF ANTAGONISTS

CROSS REFERENCE TO A RELATED APPLICATION

This application is a continuation of International Patent Application No. PCT/US2013/043452, filed on May 30, 2013, which claims the benefit from U.S. Provisional Application No. 61/653,861, filed on 31 May 2012, which is incorporated by reference herein in its entirety.

SEQUENCE LISTING

The instant application contains a Sequence Listing which has been submitted in ASCII format via EFS-Web and is hereby incorporated by reference in its entirety. Said ASCII copy, created on Nov. 17, 2014, is named P4926R1C1SeqListing.txt and is 14,299 bytes in size.

BACKGROUND OF THE INVENTION

The provision of two distinct signals to T-cells is a widely accepted model for lymphocyte activation of resting T lymphocytes by antigen-presenting cells (APCs). Lafferty et al, Aust. J. Exp. Biol. Med. ScL 53: 27-42 (1975). This model further provides for the discrimination of self from non-self and immune tolerance. Bretscher et al, Science 169: 1042-1049 (1970); Bretscher, P. A., P.N.A.S. USA 96: 185-190 (1999); Jenkins et al, J. Exp. Med. 165: 302-319 (1987). The primary signal, or antigen specific signal, is transduced through the T-cell receptor (TCR) following recognition of foreign antigen peptide presented in the context of the major histocompatibility-complex (MHC). The second or co-stimulatory signal is delivered to T-cells by co-stimulatory molecules expressed on antigen-presenting cells (APCs), and induce T-cells to promote clonal expansion, cytokine secretion and effector function. Lenschow et al., Ann. Rev. Immunol. 14:233 (1996). In the absence of co-stimulation, T-cells can become refractory to antigen stimulation, do not mount an effective immune response, and further may result in exhaustion or tolerance to foreign antigens.

In the two-signal model T-cells receive both positive and negative secondary co-stimulatory signals. The regulation of such positive and negative signals is critical to maximize the host's protective immune responses, while maintaining immune tolerance and preventing autoimmunity. Negative secondary signals seem necessary for induction of T-cell tolerance, while positive signals promote T-cell activation. While the simple two-signal model still provides a valid explanation for naive lymphocytes, a host's immune response is a dynamic process, and co-stimulatory signals can also be provided to antigen-exposed T-cells. The mechanism of co-stimulation is of therapeutic interest because the manipulation of co-stimulatory signals has shown to provide a means to either enhance or terminate cell-based immune response. Recently, it has been discovered that T cell dysfunction or anergy occurs concurrently with an induced and sustained expression of the inhibitory receptor, programmed death 1 polypeptide (PD-1). As a result, therapeutic targeting of PD-1 and other molecules which signal through interactions with PD-1, such as programmed death ligand 1 (PD-L1) and programmed death ligand 2 (PD-L2) are an area of intense interest.

PD-L1 is overexpressed in many cancers and is often associated with poor prognosis (Okazaki T et al., Intern. Immun. 2007 19(7):813) (Thompson R H et al., Cancer Res 2006, 66(7):3381). Interestingly, the majority of tumor infiltrating T lymphocytes predominantly express PD-1, in contrast to T lymphocytes in normal tissues and peripheral blood T lymphocytes indicating that up-regulation of PD-1 on tumor-reactive T cells can contribute to impaired antitumor immune responses (Blood 2009 114(8):1537). This may be due to exploitation of PD-L1 signaling mediated by PD-L1 expressing tumor cells interacting with PD-1 expressing T cells to result in attenuation of T cell activation and evasion of immune surveillance (Sharpe et al., Nat Rev 2002) (Keir M E et al., 2008 Annu. Rev. Immunol. 26:677). Therefore, inhibition of the PD-L1/PD-1 interaction may enhance CD8+ T cell-mediated killing of tumors.

The inhibition of PD-1 axis signaling through its direct ligands (e.g., PD-L1, PD-L2) has been proposed as a means to enhance T cell immunity for the treatment of cancer (e.g., tumor immunity). Moreover, similar enhancements to T cell immunity have been observed by inhibiting the binding of PD-L1 to the binding partner B7-1. Optimal therapeutic treatment could combine blockade of PD-1 receptor/ligand interaction with other anti-cancer agents. There remains a need for such an optimal therapy for treating, stabilizing, preventing, and/or delaying development of various cancers.

All references, publications, and patent applications disclosed herein are hereby incorporated by reference in their entirety.

BRIEF SUMMARY OF THE INVENTION

The present invention describes a combination treatment comprising oxaliplatin, leucovorin and 5-FU and a PD-1 axis binding antagonist with or without a VEGF antagonist.

Provided herein are methods for treating cancer or slowing progression of cancer in an individual comprising administering to the individual an effective amount of a PD-1 axis binding antagonist and oxaliplatin, leucovorin and 5-FU. In some aspects the method further comprises administering a VEGF antagonist.

The cancer may be a melanoma, a colorectal cancer, a non-small cell lung cancer, an ovarian cancer, a breast cancer, a prostate cancer, a pancreatic cancer, hematological malignancy or a renal cell carcinoma. The cancer may be at early stage or at late stage. In some embodiments, the subject treated is a human.

In some embodiments, the treatment results in sustained response in the individual after cessation of the treatment. In some embodiments, the treatment produces a complete response, a partial response, or stable disease in the subject.

In some embodiments, the PD-1 axis binding antagonist is a PD-1 binding antagonist, a PD-L1 binding antagonist or a PD-L2 binding antagonist. In some embodiments, the PD-1 binding antagonist inhibits binding of PD-1 to PD-L1 and/or binding of PD-1 to PD-L2. In some embodiments, the PD-1 binding antagonist is an antibody (e.g., antibody MDX-1106, CT-011 and Merck 3745 described herein), an antigen binding fragments thereof, an immunoadhesin, a fusion protein, or an oligopeptide. In some embodiments, the PD-L1 binding antagonist inhibits binding of PD-L1 to PD-1 and/or binding of PD-L1 to B7-1. In some embodiments, the PD-L1 binding antagonist is an antibody (e.g., antibody YW243.55.570 and MDX-1105 described herein), an antigen binding fragments thereof, an immunoadhesin, a fusion protein, or an oligopeptide. In some embodiments, the PD-L2 binding antagonist inhibits binding of PD-L2 to PD-1. In some embodiments, the PD-L2 binding antagonist is an antibody, an antigen binding fragments thereof, an immunoadhesin (e.g., AMP-224 described herein), a fusion protein, or an oligopeptide.

In some embodiments, the VEGF antagonist is an antibody, e.g., a monoclonal antibody. In some embodiments the anti-VEGF antibody binds the same epitope as the monoclonal anti-VEGF antibody A4.6.1 produced by hybridoma ATCC HB 10709. The anti-VEGF antibody may be a humanized antibody or a human antibody. In some embodiments the anti-VEGF antibody is bevacizumab. In some embodiments the anti-VEGF antibody has a heavy chain variable region comprising the following amino acid sequence:

```
                                          (SEQ ID NO: 22)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT VSS
``` and a light chain variable region comprising the following amino acid sequence:

```
                                          (SEQ ID NO: 23)
 DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

In another aspect, provided is a kit comprising a PD-1 axis binding antagonist, oxaliplatin, leucovorin and 5-FU with or without a VEGF antagonist for treating or delaying progression of a cancer in an individual or enhancing immune function in an individual having cancer. The kit may comprise a PD-1 axis binding antagonist and a package insert comprising instructions for using the PD-1 axis binding antagonist in combination with oxaliplatin, leucovorin and 5-FU with or without a VEGF antagonist to treat or delay progression of cancer in an individual, or enhancing immune function in an individual having cancer. The kit may comprise a VEGF antagonist and a package insert comprising instructions for using the VEGF antagonist in combination with a PD-1 axis binding antagonist and oxaliplatin, leucovorin and 5-FU to treat or delay progression of cancer in an individual, or to enhance immune function in an individual having cancer. The kit may comprise a PD-1 axis binding antagonist and a VEGF antagonist, and a package insert comprising instructions for using the PD-1 axis binding antagonist and the VEGF antagonist to treat or delay progression of cancer in an individual, or to enhance immune function in an individual having cancer.

DETAILED DESCRIPTION OF THE INVENTION

I. General Techniques

Figure 1:
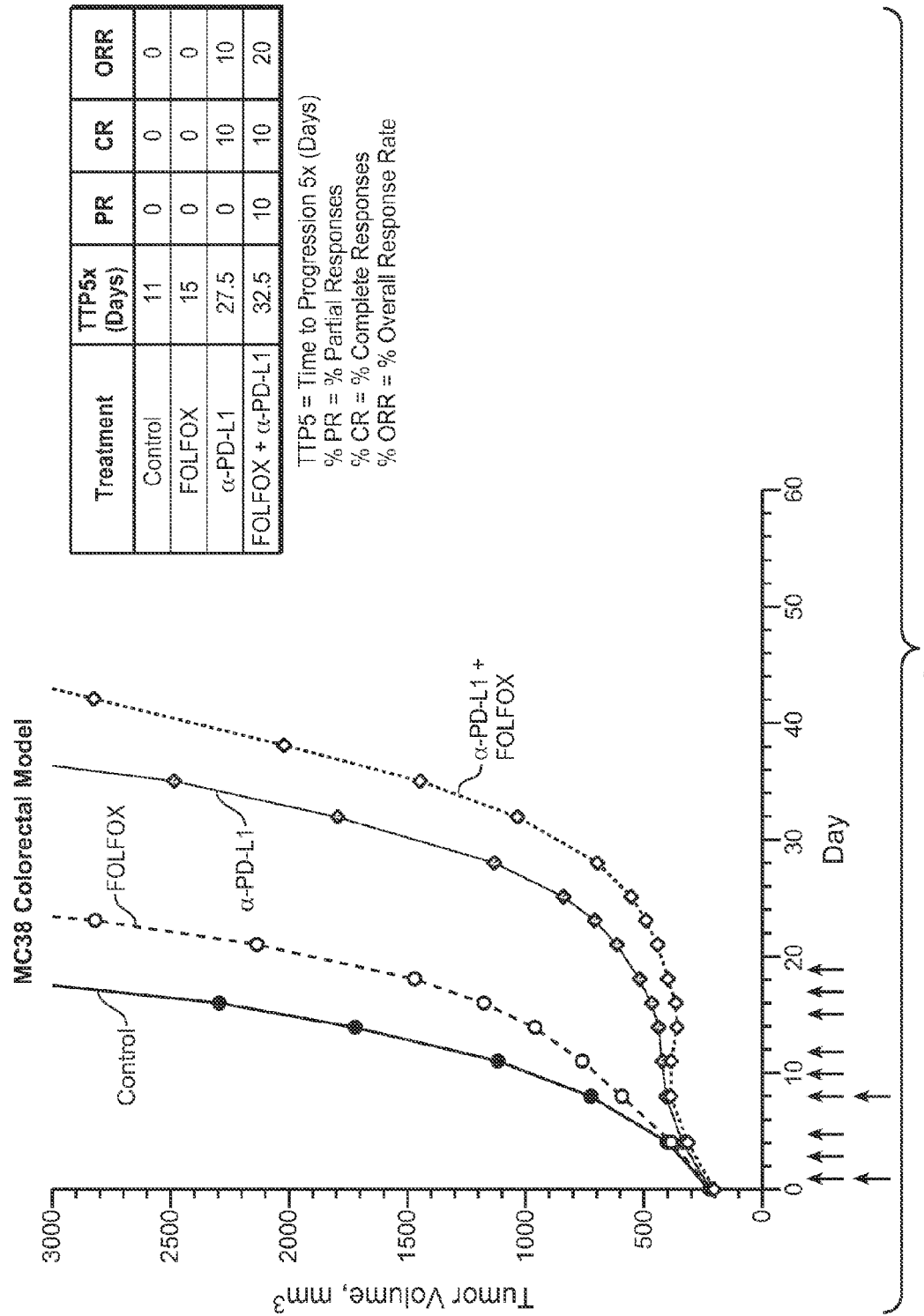
FIG. 1 is a graph depicting changes in tumor volume with anti-PD-L1 antibodies and FOLFOX co-treatment. The data demonstrate a significant reduction of tumor growth and sustained anti-tumor effect as compared to anti-PD-L1 antibodies or FOLFOX treatment alone.
Figure 2:
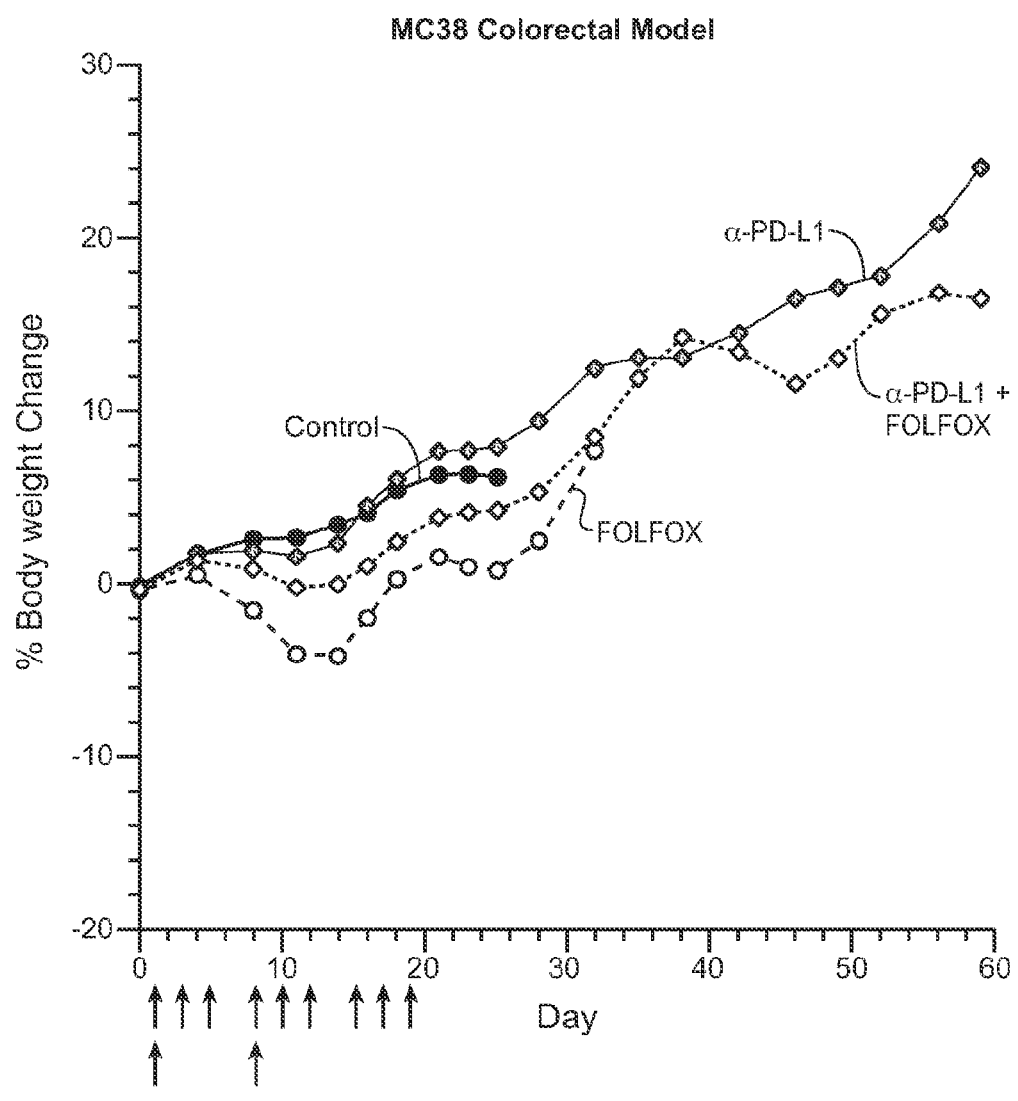
FIG. 2 is a graph showing changes in body weight for the treatment groups shown in FIG. 1.
Figure 3:
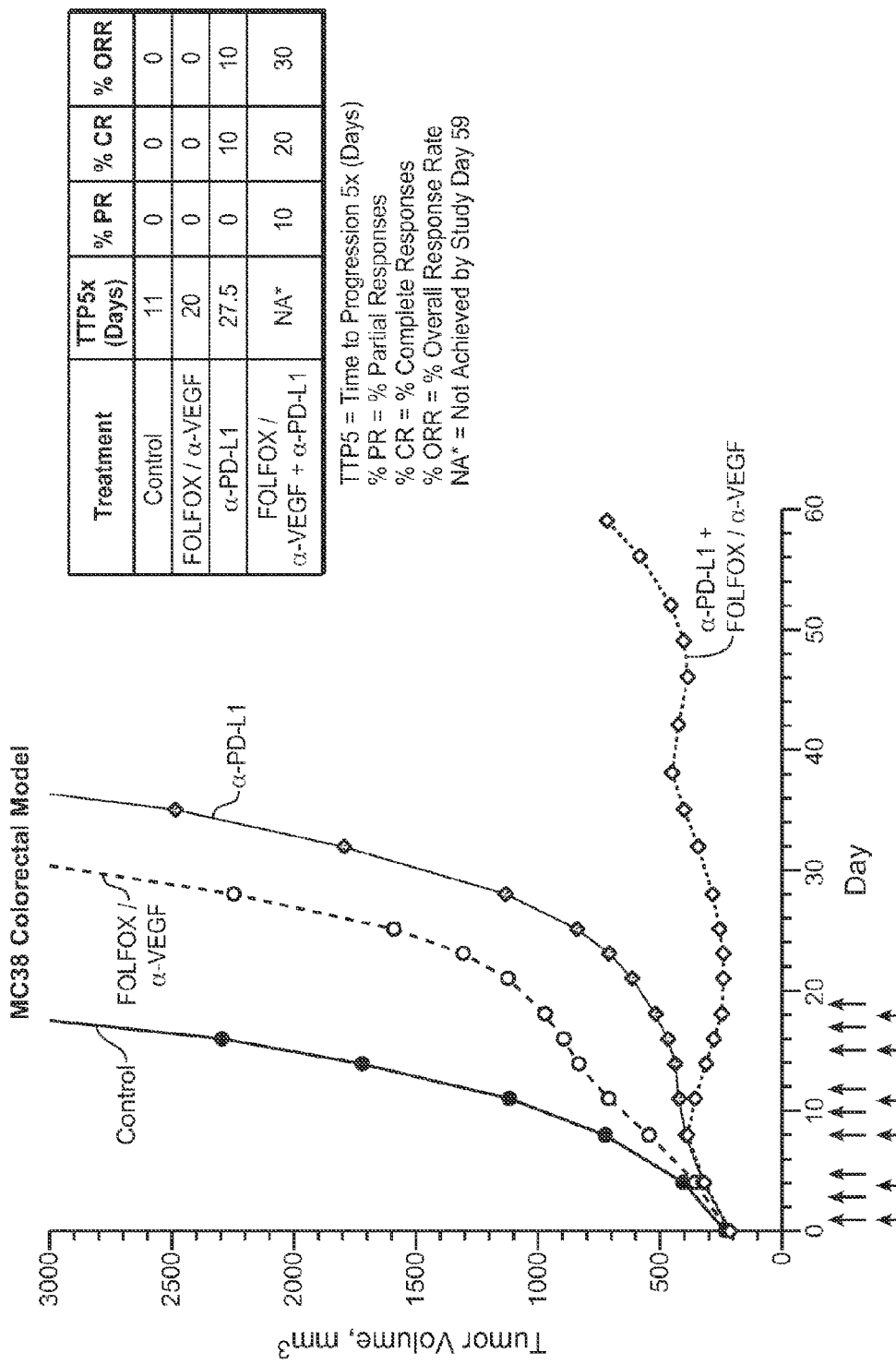
FIG. 3 is a graph depicting changes in tumor volume with anti-PD-L1 antibodies in combination with FOLFOX as compared to anti-PD-L1 antibodies in combination with FOLFOX and anti-VEGF antibody. The data demonstrate that additional administration of anti-VEGF antibody significantly reduced tumor growth and resulted in a sustained anti-tumor effect as compared to treatment with anti-PD-L1 antibodies in combination with FOLFOX.

The techniques and procedures described or referenced herein are generally well understood and commonly employed using conventional methodology by those skilled in the art, such as, for example, the widely utilized methodologies described in Sambrook et al., *Molecular Cloning: A Laboratory Manual* 3d edition (2001) Cold Spring Harbor Laboratory Press, Cold Spring Harbor, N.Y.; *Current Protocols in Molecular Biology* (F. M. Ausubel, et al. eds., (2003)); the series *Methods in Enzymology* (Academic Press, Inc.): *PCR 2: A Practical Approach* (M. J. MacPherson, B. D. Hames and G. R. Taylor eds. (1995)), Harlow and Lane, eds. (1988) *Antibodies, A Laboratory Manual*, and *Animal Cell Culture* (R. I. Freshney, ed. (1987)); *Oligonucleotide Synthesis* (M. J. Gait, ed., 1984); *Methods in Molecular Biology*, Humana Press; *Cell Biology: A Laboratory Notebook* (J. E. Cellis, ed., 1998) Academic Press; *Animal Cell Culture* (R. I. Freshney), ed., 1987); *Introduction to Cell and Tissue Culture* (J. P. Mather and P. E. Roberts, 1998) Plenum Press; *Cell and Tissue Culture: Laboratory Procedures* (A. Doyle, J. B. Griffiths, and D. G. Newell, eds., 1993-8) J. Wiley and Sons; *Handbook of Experimental Immunology* (D. M. Weir and C. C. Blackwell, eds.); *Gene Transfer Vectors for Mammalian Cells* (J. M. Miller and M. P. Calos, eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: A Practical Approach* (D. Catty, ed., IRL Press, 1988-1989); *Monoclonal Antibodies: A Practical Approach* (P. Shepherd and C. Dean, eds., Oxford University Press, 2000); *Using Antibodies: A Laboratory Manual* (E. Harlow and D. Lane (Cold Spring Harbor Laboratory Press, 1999); *The Antibodies* (M. Zanetti and J. D. Capra, eds., Harwood Academic Publishers, 1995); and *Cancer: Principles and Practice of Oncology* (V. T. DeVita et al., eds., J. B. Lippincott Company, 1993).

II. Definitions

The term "PD-1 axis binding antagonist" is a molecule that inhibits the interaction of a PD-1 axis binding partner with either one or more of its binding partner, so as to remove T-cell dysfunction resulting from signaling on the PD-1 signaling axis—with a result being to restore or enhance T-cell function. As used herein, a PD-1 axis binding antagonist includes a PD-1 binding antagonist, a PD-L1 binding antagonist and a PD-L2 binding antagonist.

The term "PD-1 binding antagonists" is a molecule that decreases, blocks, inhibits, abrogates or interferes with signal transduction resulting from the interaction of PD-1 with one or more of its binding partners, such as PD-L1, PD-L2. In some embodiments, the PD-1 binding antagonist is a molecule that inhibits the binding of PD-1 to its binding partners. In a specific aspect, the PD-1 binding antagonist inhibits the binding of PD-1 to PD-L1 and/or PD-L2. For example, PD-1 binding antagonists include anti-PD-1 antibodies, antigen binding fragments thereof, immunoadhesins, fusion proteins, oligopeptides and other molecules that decrease, block, inhibit, abrogate or interfere with signal transduction resulting from the interaction of PD-1 with PD-L1 and/or PD-L2. In one embodiment, a PD-1 binding antagonist reduces the negative co-stimulatory signal mediated by or through cell surface proteins expressed on T lymphocytes mediated signaling through PD-1 so as render a dysfunctional T-cell less non-dysfunctional. In some embodiments, the PD-1 binding antagonist is an anti-PD-1 antibody. In a specific aspect, a PD-1 binding antagonist is MDX-1106 described herein. In another specific aspect, a PD-1 binding antagonist is Merck 3745 described herein. In another specific aspect, a PD-1 binding antagonist is CT-011 described herein.

The term "PD-L1 binding antagonists" is a molecule that decreases, blocks, inhibits, abrogates or interferes with signal transduction resulting from the interaction of PD-L1 with either one or more of its binding partners, such as PD-1, B7-1. In some embodiments, a PD-L1 binding antagonist is a molecule that inhibits the binding of PD-L1 to its binding partners. In a specific aspect, the PD-L1 binding antagonist inhibits binding of PD-L1 to PD-1 and/or B7-1. In some embodiments, the PD-L1 binding antagonists include anti-PD-L1 antibodies, antigen binding fragments thereof, immunoadhesins, fusion proteins, oligopeptides and other molecules that decrease, block, inhibit, abrogate or interfere with signal transduction resulting from the interaction of PD-L1 with one or more of its binding partners, such as PD-1, B7-1. In one embodiment, a PD-L1 binding antagonist reduces the negative co-stimulatory signal mediated by or through cell surface proteins expressed on T lymphocytes mediated signaling through PD-L1 so as render a dysfunctional T-cell less non-dysfunctional. In some embodiments, a PD-L1 binding antagonist is an anti-PD-L1 antibody. In a specific aspect, an anti-PD-L1 antibody is YW243.55.S70 described herein. In another specific aspect, an anti-PD-L1 antibody is MDX-1105 described herein.

The term "PD-L2 binding antagonists" is a molecule that decreases, blocks, inhibits, abrogates or interferes with signal transduction resulting from the interaction of PD-L2 with either one or more of its binding partners, such as PD-1. In some embodiments, a PD-L2 binding antagonist is a molecule that inhibits the binding of PD-L2 to its binding partners. In a specific aspect, the PD-L2 binding antagonist inhibits binding of PD-L2 to PD-1. In some embodiments, the PD-L2 antagonists include anti-PD-L2 antibodies, antigen binding fragments thereof, immunoadhesins, fusion proteins, oligopeptides and other molecules that decrease, block, inhibit, abrogate or interfere with signal transduction resulting from the interaction of PD-L2 with either one or more of its binding partners, such as PD-1. In one embodiment, a PD-L2 binding antagonist reduces the negative co-stimulatory signal mediated by or through cell surface proteins expressed on T lymphocytes mediated signaling through PD-L2 so as render a dysfunctional T-cell less non-dysfunctional. In some embodiments, a PD-L2 binding antagonist is a PD-L2 immunoadhesin. In a specific aspect, a PD-L2 immunoadhesin is AMP-224 described herein.

A "VEGF antagonist" refers to a molecule capable of neutralizing, blocking, inhibiting, abrogating, reducing or interfering with VEGF activities including its binding to one or more VEGF receptors. VEGF antagonists include anti-VEGF antibodies and antigen-binding fragments thereof, receptor molecules and derivatives which bind specifically to VEGF thereby sequestering its binding to one or more receptors, anti-VEGF receptor antibodies and VEGF receptor antagonists such as small molecule inhibitors of the VEGFR tyrosine kinases.

The term "VEGF" or "VEGF-A" is used to refer to the 165-amino acid human vascular endothelial cell growth factor and related 121-, 145-, 189-, and 206-amino acid human vascular endothelial cell growth factors, as described by, e.g., Leung et al. Science, 246:1306 (1989), and Houck et al. Mol. Endocrin., 5:1806 (1991), together with the naturally occurring allelic and processed forms thereof. VEGF-A is part of a gene family including VEGF-B, VEGF-C, VEGF-D, VEGF-E, VEGF-F, and PlGF. VEGF-A primarily binds to two high affinity receptor tyrosine kinases, VEGFR-1 (Flt-1) and VEGFR-2 (Flk-1/KDR), the latter being the major transmitter of vascular endothelial cell mitogenic signals of VEGF-A. Additionally, neuropilin-1 has been identified as a receptor for heparin-binding VEGF-A isoforms, and may play a role in vascular development. The term "VEGF" or "VEGF-A" also refers to VEGFs from non-human species such as mouse, rat, or primate. Sometimes the VEGF from a specific species is indicated by terms such as hVEGF for human VEGF or mVEGF for murine VEGF. The term "VEGF" is also used to refer to truncated forms or fragments of the polypeptide comprising amino acids 8 to 109 or 1 to 109 of the 165-amino acid human vascular endothelial cell growth factor. Reference to any such forms of VEGF may be identified in the present application, e.g., by "VEGF (8-109)," "VEGF (1-109)" or "VEGF165." The amino acid positions for a "truncated" native VEGF are numbered as indicated in the native VEGF sequence. For example, amino acid position 17 (methionine) in truncated native VEGF is also position 17 (methionine) in native VEGF. The truncated native VEGF has binding affinity for the KDR and Flt-1 receptors comparable to native VEGF.

An "anti-VEGF antibody" is an antibody that binds to VEGF with sufficient affinity and specificity. The antibody selected will normally have a binding affinity for VEGF, for example, the antibody may bind hVEGF with a Kd value of between 100 nM-1 pM. Antibody affinities may be determined by a surface plasmon resonance based assay (such as the BIAcore assay as described in PCT Application Publication No. WO2005/012359); enzyme-linked immunoabsorbent assay (ELISA); and competition assays (e.g. RIA's), for example. In certain embodiments, the anti-VEGF antibody of the invention can be used as a therapeutic agent in targeting and interfering with diseases or conditions wherein the VEGF activity is involved. Also, the antibody may be subjected to other biological activity assays, e.g., in order to evaluate its effectiveness as a therapeutic. Such assays are known in the art and depend on the target antigen and intended use for the antibody. Examples include the HUVEC inhibition assay; tumor cell growth inhibition assays (as described in WO 89/06692, for example); antibody-dependent cellular cytotoxicity (ADCC) and complement-mediated cytotoxicity (CDC) assays (U.S. Pat. No. 5,500,362); and agonistic activity or hematopoiesis assays (see WO 95/27062). An anti-VEGF antibody will usually not bind to other VEGF homologues such as VEGF-B or VEGF-C, nor other growth factors such as PlGF, PDGF or bFGF.

A "chimeric VEGF receptor protein" is a VEGF receptor molecule having amino acid sequences derived from at least two different proteins, at least one of which is as VEGF receptor protein. In certain embodiments, the chimeric VEGF receptor protein is capable of binding to and inhibiting the biological activity of VEGF.

An "anti-angiogenesis agent" or "angiogenesis inhibitor" refers to a small molecular weight substance, a polynucleotide, a polypeptide, an isolated protein, a recombinant protein, an antibody, or conjugates or fusion proteins thereof, that inhibits angiogenesis, vasculogenesis, or undesirable vascular permeability, either directly or indirectly. It should be understood that the anti-angiogenesis agent includes those agents that bind and block the angiogenic activity of the angiogenic factor or its receptor. For example, an anti-angiogenesis agent is an antibody or other antagonist to an angiogenic agent as defined above, e.g., antibodies to VEGF-A or to the VEGF-A receptor (e.g., KDR receptor or Flt-1 receptor), anti-PDGFR inhibitors such as Gleevec™ (Imatinib Mesylate). Anti-angiogenesis agents also include native angiogenesis inhibitors, e.g., angiostatin, endostatin, etc. See, e.g., Klagsbrun and D'Amore, *Annu. Rev. Physiol.,* 53:217-39 (1991); Streit and Detmar, *Oncogene,* 22:3172-3179 (2003) (e.g., Table 3 listing anti-angiogenic therapy in malignant melanoma); Ferrara & Alitalo, *Nature Medicine* 5:1359-1364 (1999); Tonini et al., *Oncogene,* 22:6549-6556 (2003) (e.g., Table 2 listing known antiangiogenic factors); and Sato. *Int. J. Clin. Oncol.,* 8:200-206 (2003) (e.g., Table 1 lists anti-angiogenic agents used in clinical trials).

The term "dysfunction" in the context of immune dysfunction, refers to a state of immune reduced responsiveness to antigenic stimulation. The term includes the common elements of both exhaustion and/or anergy in which antigen recognition may occur, but the ensuing immune response is ineffective to control infection or tumor growth.

"Enhancing T-cell function" means to induce, cause or stimulate a T-cell to have a sustained or amplified biological function, or renew or reactivate exhausted or inactive T-cells. Examples of enhancing T-cell function include: increased secretion of γ-interferon from CD8$^+$ T-cells, increased proliferation, increased antigen responsiveness (e.g., viral or pathogen clearance) relative to such levels before the intervention. In one embodiment, the level of enhancement is as least 50%, alternatively 60%, 70%, 80%, 90%, 100%, 120%, 150%, 200%. The manner of measuring this enhancement is known to one of ordinary skill in the art.

A "T cell dysfunctional disorder" is a disorder or condition of T-cells characterized by decreased responsiveness to antigenic stimulation. In a particular embodiment, a T-cell dysfunctional disorder is a disorder that is specifically associated with inappropriate increased signaling through PD-1. In another embodiment, T-cell dysfunctional disorder is one in which T-cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

"Immunogenecity" refers to the ability of a particular substance to provoke an immune response. Tumors are immunogenic and enhancing tumor immunogenicity aids in the clearance of the tumor cells by the immune response. Examples of enhancing tumor immunogenicity include treatment with anti-PDL antibodies oxaliplatin, leucovorin and 5-FU with or without a VEGF antagonist.

"Sustained response" refers to the sustained effect on reducing tumor growth after cessation of a treatment. For example, the tumor size may remain to be the same or smaller as compared to the size at the beginning of the administration phase. In some embodiments, the sustained response has a duration at least the same as the treatment duration, at least 1.5×, 2.0×, 2.5×, or 3.0× length of the treatment duration.

The term "antibody" includes monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ and c isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology,* 8th Edition, Daniel P. Sties, Abba I. Terr and Tristram G. Parsolw (eds), Appleton & Lange, Norwalk, Conn., 1994, page 71 and Chapter 6. The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2A, IgG2B, IgG3, IgG4, IgA1 and IgA2.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "variable" refers to the fact that certain segments of the variable domains differ extensively in sequence among antibodies. The V domain mediates antigen binding and defines the specificity of a particular antibody for its particular antigen. However, the variability is not evenly distributed across the entire span of the variable domains. Instead, it is concentrated in three segments called hypervariable regions (HVRs) both in the light-chain and the heavy chain variable domains. The more highly conserved portions of variable domains are called the framework regions (FR). The variable domains of native heavy and light chains each comprise four FR regions, largely adopting a beta-sheet configuration, connected by three HVRs, which form loops connecting, and in some cases forming part of, the beta-sheet structure. The HVRs in each chain are held together in close proximity by the FR regions and, with the HVRs from the other chain, contribute to the formation of the antigen binding site of antibodies (see Kabat et al., *Sequences of Immunological Interest*, Fifth Edition, National Institute of Health, Bethesda, Md. (1991)). The constant domains are not involved directly in the binding of antibody to an antigen, but exhibit various effector functions, such as participation of the antibody in antibody-dependent cellular toxicity.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic site. In contrast to polyclonal antibody preparations which typically include different antibodies directed against different determinants (epitopes), each monoclonal antibody is directed against a single determinant on the antigen. In addition to their specificity, the monoclonal antibodies are advantageous in that they are synthesized by the hybridoma culture, uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein., *Nature*, 256:495-97 (1975); Hongo et al., *Hybridoma*, 14 (3): 253-260 (1995), Harlow et al., *Antibodies: A Laboratory Manual*, (Cold Spring Harbor Laboratory Press, 2$^{nd}$ ed. 1988); Hammerling et al., in: *Monoclonal Antibodies and T-Cell Hybridomas* 563-681 (Elsevier, N.Y., 1981)), recombinant DNA methods (see, e.g., U.S. Pat. No. 4,816,567), phage-display technologies (see, e.g., Clackson et al., *Nature*, 352: 624-628 (1991); Marks et al., *J. Mol. Biol.* 222: 581-597 (1992); Sidhu et al., *J. Mol. Biol.* 338(2): 299-310 (2004); Lee et al., *J. Mol. Biol.* 340(5): 1073-1093 (2004); Fellouse, *Proc. Natl. Acad. Sci. USA* 101(34): 12467-12472 (2004); and Lee et al., *J. Immunol. Methods* 284(1-2): 119-132 (2004), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., *Proc. Natl. Acad. Sci. USA* 90: 2551 (1993); Jakobovits et al., *Nature* 362: 255-258 (1993); Bruggemann et al., *Year in Immunol.* 7:33 (1993); U.S. Pat. Nos. 5,545,807; 5,545,806; 5,569,825; 5,625,126; 5,633,425; and 5,661,016; Marks et al., *Bio/Technology* 10: 779-783 (1992); Lonberg et al., *Nature* 368: 856-859 (1994); Morrison, *Nature* 368: 812-813 (1994); Fishwild et al., *Nature Biotechnol.* 14: 845-851 (1996); Neuberger, *Nature Biotechnol.* 14: 826 (1996); and Lonberg and Huszar, *Intern. Rev. Immunol.* 13: 65-93 (1995).

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, preferably the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments. Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. F(ab')$_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the $V_H$ and $V_L$ antibody domains connected into a single polypeptide chain. Preferably, the sFv polypeptide further comprises a polypeptide linker between the $V_H$ and $V_L$ domains which enables the sFv to form the desired structure for antigen binding. For a review of the sFv, see Pluckthun in *The Pharmacology of*

*Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fc region of an antibody which retains or has modified FcR binding capability. Examples of antibody fragments include linear antibody, single-chain antibody molecules and multispecific antibodies formed from antibody fragments.

The term "diabodies" refers to small antibody fragments prepared by constructing sFv fragments (see preceding paragraph) with short linkers (about 5-10) residues) between the $V_H$ and $V_L$ domains such that inter-chain but not intra-chain pairing of the V domains is achieved, thereby resulting in a bivalent fragment, i.e., a fragment having two antigen-binding sites. Bispecific diabodies are heterodimers of two "crossover" sFv fragments in which the $V_H$ and $V_L$ domains of the two antibodies are present on different polypeptide chains. Diabodies are described in greater detail in, for example, EP 404,097; WO 93/11161; Hollinger et al., *Proc. Natl. Acad. Sci. USA* 90: 6444-6448 (1993).

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is(are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA*, 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR (hereinafter defined) of the recipient are replaced by residues from an HVR of a non-human species (donor antibody) such as mouse, rat, rabbit or non-human primate having the desired specificity, affinity, and/or capacity. In some instances, framework ("FR") residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. The number of these amino acid substitutions in the FR are typically no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332:323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409.

A "human antibody" is an antibody that possesses an amino-acid sequence corresponding to that of an antibody produced by a human and/or has been made using any of the techniques for making human antibodies as disclosed herein. This definition of a human antibody specifically excludes a humanized antibody comprising non-human antigen-binding residues. Human antibodies can be produced using various techniques known in the art, including phage-display libraries. Hoogenboom and Winter, *J. Mol. Biol.*, 227: 381 (1991); Marks et al., *J. Mol. Biol.*, 222:581 (1991). Also available for the preparation of human monoclonal antibodies are methods described in Cole et al., *Monoclonal Antibodies and Cancer Therapy*, Alan R. Liss, p. 77 (1985); Boerner et al., *J. Immunol.*, 147(1):86-95 (1991). See also van Dijk and van de Winkel, *Curr. Opin. Pharmacol.*, 5: 368-74 (2001). Human antibodies can be prepared by administering the antigen to a transgenic animal that has been modified to produce such antibodies in response to antigenic challenge, but whose endogenous loci have been disabled, e.g., immunized xenomice (see, e.g., U.S. Pat. Nos. 6,075,181 and 6,150,584 regarding XENOMOUSE™ technology). See also, for example, Li et al., *Proc. Natl. Acad. Sci. USA*, 103:3557-3562 (2006) regarding human antibodies generated via a human B-cell hybridoma technology.

The term "hypervariable region," "HVR," or "HV," when used herein refers to the regions of an antibody variable domain which are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al., *Immunity* 13:37-45 (2000); Johnson and Wu, in *Methods in Molecular Biology* 248:1-25 (Lo, ed., Human Press, Totowa, N.J., 2003). Indeed, naturally occurring camelid antibodies consisting of a heavy chain only are functional and stable in the absence of light chain. See, e.g., Hamers-Casterman et al., *Nature* 363:446-448 (1993); Sheriff et al., *Nature Struct. Biol.* 3:733-736 (1996).

A number of HVR delineations are in use and are encompassed herein. The Kabat Complementarity Determining Regions (CDRs) are based on sequence variability and are the most commonly used (Kabat et al., *Sequences of Proteins of Immunological Interest*, 5th Ed. Public Health Service, National Institutes of Health, Bethesda, Md. (1991)). Chothia refers instead to the location of the structural loops (Chothia and Lesk, *J. Mol. Biol.* 196:901-917 (1987)). The AbM HVRs represent a compromise between the Kabat HVRs and Chothia structural loops, and are used by Oxford Molecular's AbM antibody modeling software. The "contact" HVRs are based on an analysis of the available complex crystal structures. The residues from each of these HVRs are noted below.

| Loop | Kabat | AbM | Chothia | Contact |
|------|-------|-----|---------|---------|
| L1 | L24-L34 | L24-L34 | L26-L32 | L30-L36 |
| L2 | L50-L56 | L50-L56 | L50-L52 | L46-L55 |
| L3 | L89-L97 | L89-L97 | L91-L96 | L89-L96 |
| H1 | H31-H35B | H26-H35B | H26-H32 | H30-H35B |
|    |          | (Kabat numbering) | | |
| H1 | H31-H35 | H26-H35 | H26-H32 | H30-H35 |
|    |         | (Chothia numbering) | | |
| H2 | H50-H65 | H50-H58 | H53-H55 | H47-H58 |
| H3 | H95-H102 | H95-H102 | H96-H101 | H93-H101 |

HVRs may comprise "extended HVRs" as follows: 24-36 or 24-34 (L1), 46-56 or 50-56 (L2) and 89-97 or 89-96 (L3) in the VL and 26-35 (H1), 50-65 or 49-65 (H2) and 93-102, 94-102, or 95-102 (H3) in the VH. The variable domain residues are numbered according to Kabat et al., supra, for each of these definitions.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

"Framework" or "FR" residues are those variable-domain residues other than the HVR residues as herein defined.

A "human consensus framework" or "acceptor human framework" is a framework that represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., Sequences of Proteins of Immunological Interest, 5th Ed. Public Health Service, National Institutes of Health, Bethesda, Md. (1991). Examples include for the VL, the subgroup may be subgroup kappa I, kappa II, kappa III or kappa IV as in Kabat et al., supra. Additionally, for the VH, the subgroup may be subgroup I, subgroup II, or subgroup III as in Kabat et al., supra. Alternatively, a human consensus framework can be derived from the above in which particular residues, such as when a human framework residue is selected based on its homology to the donor framework by aligning the donor framework sequence with a collection of various human framework sequences. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

A "VH subgroup III consensus framework" comprises the consensus sequence obtained from the amino acid sequences in variable heavy subgroup III of Kabat et al., supra. In one embodiment, the VH subgroup III consensus framework amino acid sequence comprises at least a portion or all of each of the following sequences:

```
                                        (SEQ ID NO: 30)
    EVQLVESGGGLVQPGGSLRLSCAAS (HC-FR1), (SEQ ID NO: 31)
    WVRQAPGKGLEWV (HC-FR2),,

SEQ ID NO: 32
    RFTISADTSKNTAYLQMNSLRAEDTAVYYCAR (HC-FR3),, (SEQ ID NO: 33)
    WGQGTLVTVSA (HC-FR4),.
```

A "VL kappa I consensus framework" comprises the consensus sequence obtained from the amino acid sequences in variable light kappa subgroup I of Kabat et al., supra. In one embodiment, the VH subgroup I consensus framework amino acid sequence comprises at least a portion or all of each of the following sequences:

```
                                        (SEQ ID NO: 34)
    DIQMTQSPSSLSASVGDRVTITC (LC-FR1), (SEQ ID NO: 35)
    WYQQKPGKAPKLLIY (LC-FR2), (SEQ ID NO: 36)
    GVPSRFSGSGSGTDFTLTISSLQPEDFATYYC (LC-FR3), (SEQ ID NO: 37)
    FGQGTKVEIKR (LC-FR4).
```

An "amino-acid modification" at a specified position, e.g. of the Fc region, refers to the substitution or deletion of the specified residue, or the insertion of at least one amino acid residue adjacent the specified residue. Insertion "adjacent" to a specified residue means insertion within one to two residues thereof. The insertion may be N-terminal or C-terminal to the specified residue. The preferred amino acid modification herein is a substitution.

An "affinity-matured" antibody is one with one or more alterations in one or more HVRs thereof that result in an improvement in the affinity of the antibody for antigen, compared to a parent antibody that does not possess those alteration(s). In one embodiment, an affinity-matured antibody has nanomolar or even picomolar affinities for the target antigen. Affinity-matured antibodies are produced by procedures known in the art. For example, Marks et al., Bio/Technology 10:779-783 (1992) describes affinity maturation by VH- and VL-domain shuffling. Random mutagenesis of HVR and/or framework residues is described by, for example: Barbas et al. Proc Nat. Acad. Sci. USA 91:3809-3813 (1994); Schier et al. Gene 169:147-155 (1995); Yelton et al. J. Immunol. 155:1994-2004 (1995); Jackson et al., J. Immunol. 154(7):3310-9 (1995); and Hawkins et al, J. Mol. Biol. 226:889-896 (1992).

As use herein, the term "specifically binds to" or is "specific for" refers to measurable and reproducible interactions such as binding between a target and an antibody, which is determinative of the presence of the target in the presence of a heterogeneous population of molecules including biological molecules. For example, an antibody that specifically binds to a target (which can be an epitope) is an antibody that binds this target with greater affinity, avidity, more readily, and/or with greater duration than it binds to other targets. In one embodiment, the extent of binding of an antibody to an unrelated target is less than about 10% of the binding of the antibody to the target as measured, e.g., by a radioimmunoassay (RIA). In certain embodiments, an antibody that specifically binds to a target has a dissociation constant (Kd) of ≤1 µM, ≤100 nM, ≤10 nM, ≤1 nM, or ≤0.1 nM. In certain embodiments, an antibody specifically binds to an epitope on a protein that is conserved among the protein from different species. In another embodiment, specific binding can include, but does not require exclusive binding.

As used herein, the term "immunoadhesin" designates antibody-like molecules which combine the binding specificity of a heterologous protein (an "adhesin") with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2 (including IgG2A and IgG2B), IgG-3, or IgG-4 subtypes, IgA (including IgA-1 and IgA-2), IgE, IgD or IgM. The Ig fusions preferably include the substitution of a domain of a polypeptide or antibody described herein in the place of at least one variable region within an Ig molecule. In a particularly preferred embodiment, the immunoglobulin fusion includes the hinge, CH2 and CH3, or the hinge, CH1, CH2 and CH3 regions of an IgG1 molecule. For the production of immunoglobulin fusions see also U.S. Pat. No. 5,428,130 issued Jun. 27, 1995. For example, useful immunoadhesins as second medicaments useful for combination therapy herein include polypeptides that comprise the extracellular or PD-1 binding portions of PD-L1 or PD-L2 or the extracellular or PD-L1 or PD-L2 binding portions of PD-1, fused to a constant domain of an immunoglobulin sequence, such as a PD-L1 ECD-Fc, a PD-L2 ECD-Fc, and a PD-1 ECD-Fc, respectively. Immunoadhesin combinations of Ig Fc and ECD of cell surface receptors are sometimes termed soluble receptors.

A "fusion protein" and a "fusion polypeptide" refer to a polypeptide having two portions covalently linked together, where each of the portions is a polypeptide having a different property. The property may be a biological property, such as activity in vitro or in vivo. The property may also be simple chemical or physical property, such as binding to a target molecule, catalysis of a reaction, etc. The two portions may be linked directly by a single peptide bond or through a peptide linker but are in reading frame with each other.

A "PD-1 oligopeptide," "PD-L1 oligopeptide," or "PD-L2 oligopeptide" is an oligopeptide that binds, preferably specifically, to a PD-1, PD-L1 or PD-L2 negative costimulatory polypeptide, respectively, including a receptor, ligand or signaling component, respectively, as described herein. Such oligopeptides may be chemically synthesized using known oligopeptide synthesis methodology or may be prepared and purified using recombinant technology. Such oligopeptides are usually at least about 5 amino acids in length, alternatively at least about 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 amino acids in length or more. Such oligopeptides may be identified using well known techniques. In this regard, it is noted that techniques for screening oligopeptide libraries for oligopeptides that are capable of specifically binding to a polypeptide target are well known in the art (see, e.g., U.S. Pat. Nos. 5,556,762, 5,750,373, 4,708,871, 4,833,092, 5,223,409, 5,403,484, 5,571,689, 5,663,143; PCT Publication Nos. WO 84/03506 and WO84/03564; Geysen et al., *Proc. Natl. Acad. Sci. U.S.A.*, 81:3998-4002 (1984); Geysen et al., *Proc. Natl. Acad. Sci. U.S.A.*, 82:178-182 (1985); Geysen et al., in Synthetic Peptides as Antigens, 130-149 (1986); Geysen et al., *J. Immunol.* Meth., 102:259-274 (1987); Schoofs et al., *J. Immunol.*, 140:611-616 (1988), Cwirla, S. E. et al. *Proc. Natl. Acad. Sci. USA*, 87:6378 (1990); Lowman, H. B. et al. *Biochemistry*, 30:10832 (1991); Clackson, T. et al. *Nature*, 352: 624 (1991); Marks, J. D. et al., *J. Mol. Biol.*, 222:581 (1991); Kang, A. S. et al. *Proc. Natl. Acad. Sci. USA*, 88:8363 (1991), and Smith, G. P., *Current Opin. Biotechnol.*, 2:668 (1991).

A "blocking" antibody or an "antagonist" antibody is one that inhibits or reduces a biological activity of the antigen it binds. In some embodiments, blocking antibodies or antagonist antibodies substantially or completely inhibit the biological activity of the antigen. For example, a VEGF-specific antagonist antibody binds VEGF and inhibits the ability of VEGF to induce vascular endothelial cell proliferation or to induce vascular permeability. The anti-PD-L1 antibodies of the invention block the signaling through PD-1 so as to restore a functional response by T-cells from a dysfunctional state to antigen stimulation.

An "agonist" or activating antibody is one that enhances or initiates signaling by the antigen to which it binds. In some embodiments, agonist antibodies cause or activate signaling without the presence of the natural ligand.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue. Suitable native-sequence Fc regions for use in the antibodies of the invention include human IgG1, IgG2 (IgG2A, IgG2B), IgG3 and IgG4.

"Fc receptor" or "FcR" describes a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors, FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see M. Daëron, *Annu. Rev. Immunol.*

15:203-234 (1997). FcRs are reviewed in Ravetch and Kinet, *Annu. Rev. Immunol.* 9: 457-92 (1991); Capel et al., *Immunomethods* 4: 25-34 (1994); and de Haas et al., *J. Lab. Clin. Med.* 126: 330-41 (1995). Other FcRs, including those to be identified in the future, are encompassed by the term "FcR" herein.

The term "Fc receptor" or "FcR" also includes the neonatal receptor, FcRn, which is responsible for the transfer of maternal IgGs to the fetus. Guyer et al., *J. Immunol.* 117: 587 (1976) and Kim et al., *J. Immunol.* 24: 249 (1994). Methods of measuring binding to FcRn are known (see, e.g., Ghetie and Ward, *Immunol. Today* 18: (12): 592-8 (1997); Ghetie et al., *Nature Biotechnology* 15 (7): 637-40 (1997); Hinton et al., *J. Biol. Chem.* 279 (8): 6213-6 (2004); WO 2004/92219 (Hinton et al.). Binding to FcRn in vivo and serum half-life of human FcRn high-affinity binding polypeptides can be assayed, e.g., in transgenic mice or transfected human cell lines expressing human FcRn, or in primates to which the polypeptides having a variant Fc region are administered. WO 2004/42072 (Presta) describes antibody variants which improved or diminished binding to FcRs. See also, e.g., Shields et al., *J. Biol. Chem.* 9(2): 6591-6604 (2001).

The phrase "substantially reduced," or "substantially different," as used herein, denotes a sufficiently high degree of difference between two numeric values (generally one associated with a molecule and the other associated with a reference/comparator molecule) such that one of skill in the art would consider the difference between the two values to be of statistical significance within the context of the biological characteristic measured by said values (e.g., Kd values). The difference between said two values is, for example, greater than about 10%, greater than about 20%, greater than about 30%, greater than about 40%, and/or greater than about 50% as a function of the value for the reference/comparator molecule.

The term "substantially similar" or "substantially the same," as used herein, denotes a sufficiently high degree of similarity between two numeric values (for example, one associated with an antibody of the invention and the other associated with a reference/comparator antibody), such that one of skill in the art would consider the difference between the two values to be of little or no biological and/or statistical significance within the context of the biological characteristic measured by said values (e.g., Kd values). The difference between said two values is, for example, less than about 50%, less than about 40%, less than about 30%, less than about 20%, and/or less than about 10% as a function of the reference/comparator value.

"Carriers" as used herein include pharmaceutically acceptable carriers, excipients, or stabilizers that are nontoxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

A "package insert" refers to instructions customarily included in commercial packages of medicaments that contain information about the indications customarily included in commercial packages of medicaments that contain information about the indications, usage, dosage, administration, contraindications, other medicaments to be combined with the packaged product, and/or warnings concerning the use of such medicaments, etc.

As used herein, the term "treatment" refers to clinical intervention designed to alter the natural course of the individual or cell being treated during the course of clinical pathology. Desirable effects of treatment include decreasing the rate of disease progression, ameliorating or palliating the disease state, and remission or improved prognosis. For example, an individual is successfully "treated" if one or more symptoms associated with cancer are mitigated or eliminated, including, but are not limited to, reducing the proliferation of (or destroying) cancerous cells, decreasing symptoms resulting from the disease, increasing the quality of life of those suffering from the disease, decreasing the dose of other medications required to treat the disease, delaying the progression of the disease, and/or prolonging survival of individuals.

As used herein, "delaying progression of a disease" means to defer, hinder, slow, retard, stabilize, and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

An "effective amount" is at least the minimum concentration required to effect a measurable improvement or prevention of a particular disorder. An effective amount herein may vary according to factors such as the disease state, age, sex, and weight of the patient, and the ability of the antibody to elicit a desired response in the individual. An effective amount is also one in which any toxic or detrimental effects of the treatment are outweighed by the therapeutically beneficial effects. For prophylactic use, beneficial or desired results include results such as eliminating or reducing the risk, lessening the severity, or delaying the onset of the disease, including biochemical, histological and/or behavioral symptoms of the disease, its complications and intermediate pathological phenotypes presenting during development of the disease. For therapeutic use, beneficial or desired results include clinical results such as decreasing one or more symptoms resulting from the disease, increasing the quality of life of those suffering from the disease, decreasing the dose of other medications required to treat the disease, enhancing effect of another medication such as via targeting, delaying the progression of the disease, and/or prolonging survival. In the case of cancer or tumor, an effective amount of the drug may have the effect in reducing the number of cancer cells; reducing the tumor size; inhibiting (i.e., slow to some extent or desirably stop) cancer cell infiltration into peripheral organs; inhibit (i.e., slow to some extent and desirably stop) tumor metastasis; inhibiting to some extent tumor growth; and/or relieving to some extent one or more of the symptoms associated with the disorder. An effective amount can be administered in one or more administrations. For purposes of this invention, an effective amount of drug, compound, or pharmaceutical composition is an amount sufficient to accomplish prophylactic or therapeutic treatment either directly or indirectly. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

As used herein, "in conjunction with" refers to administration of one treatment modality in addition to another treatment modality. As such, "in conjunction with" refers to administration of one treatment modality before, during, or after administration of the other treatment modality to the individual.

The terms "cancer" and "cancerous" refer to or describe the physiological condition in mammals that is typically characterized by unregulated cell growth. Included in this definition are benign and malignant cancers as well as dormant tumors or micrometastatses. Examples of cancer include but are not limited to, carcinoma, lymphoma, blastoma, sarcoma, and leukemia. More particular examples of such cancers include squamous cell cancer, lung cancer (including small-cell lung cancer, non-small cell lung cancer, adenocarcinoma of the lung, and squamous carcinoma of the lung), cancer of the peritoneum, hepatocellular cancer, gastric or stomach cancer (including gastrointestinal cancer), pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney or renal cancer, liver cancer, prostate cancer, vulval cancer, thyroid cancer, hepatic carcinoma and various types of head and neck cancer, as well as B-cell lymphoma (including low grade/follicular non-Hodgkin's lymphoma (NHL); small lymphocytic (SL) NHL; intermediate grade/follicular NHL; intermediate grade diffuse NHL; high grade immunoblastic NHL; high grade lymphoblastic NHL; high grade small non-cleaved cell NHL; bulky disease NHL; mantle cell lymphoma; AIDS-related lymphoma; and Waldenstrom's Macroglobulinemia); chronic lymphocytic leukemia (CLL); acute lymphoblastic leukemia (ALL); Hairy cell leukemia; chronic myeloblastic leukemia; and post-transplant lymphoproliferative disorder (PTLD), as well as abnormal vascular proliferation associated with phakomatoses, edema (such as that associated with brain tumors), and Meigs' syndrome.

By "metastasis" is meant the spread of cancer from its primary site to other places in the body. Cancer cells can break away from a primary tumor, penetrate into lymphatic and blood vessels, circulate through the bloodstream, and grow in a distant focus (metastasize) in normal tissues elsewhere in the body. Metastasis can be local or distant. Metastasis is a sequential process, contingent on tumor cells breaking off from the primary tumor, traveling through the bloodstream, and stopping at a distant site. At the new site, the cells establish a blood supply and can grow to form a life-threatening mass. Both stimulatory and inhibitory molecular pathways within the tumor cell regulate this behavior, and interactions between the tumor cell and host cells in the distant site are also significant.

By "subject" is meant a mammal, including, but not limited to, a human or non-human mammal, such as a bovine, equine, canine, ovine, or feline. Preferably, the subject is a human. Patients are also subjects herein.

As used herein, "complete response" or "CR" refers to disappearance of all target lesions; "partial response" or "PR" refers to at least a 30% decrease in the sum of the longest diameters (SLD) of target lesions, taking as reference the baseline SLD; and "stable disease" or "SD" refers to neither sufficient shrinkage of target lesions to qualify for PR, nor sufficient increase to qualify for PD, taking as reference the smallest SLD since the treatment started.

As used herein, "progressive disease" or "PD" refers to at least a 20% increase in the SLD of target lesions, taking as reference the smallest SLD recorded since the treatment started or the presence of one or more new lesions.

As used herein, "progression free survival" (PFS) refers to the length of time during and after treatment during which the disease being treated (e.g., cancer) does not get worse. Progression-free survival may include the amount of time patients have experienced a complete response or a partial response, as well as the amount of time patients have experienced stable disease.

As used herein, "overall response rate" (ORR) refers to the sum of complete response (CR) rate and partial response (PR) rate.

As used herein, "overall survival" refers to the percentage of individuals in a group who are likely to be alive after a particular duration of time.

A "chemotherapeutic agent" is a chemical compound useful in the treatment of cancer. Examples of chemotherapeutic agents include alkylating agents such as thiotepa and cyclophosphamide (CYTOXAN®); alkyl sulfonates such as busulfan, improsulfan, and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL®); beta-lapachone; lapachol; colchicines; betulinic acid; a camptothecin (including the synthetic analogue topotecan (HYCAMTIN®), CPT-11 (irinotecan, CAMPTOSAR®), acetylcamptothecin, scopolectin, and 9-aminocamptothecin); bryostatin; pemetrexed; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; TLK-286; CDP323, an oral alpha-4 integrin inhibitor; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e. g., calicheamicin, especially calicheamicin gamma1I and calicheamicin omega1I (see, e.g., Nicolaou et al., *Angew. Chem Intl. Ed. Engl.*, 33: 183-186 (1994)); dynemicin, including dynemicin A; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN®, morpholino-doxorubicin, cyanomorpholino-doxorubicin, 2-pyrrolino-doxorubicin, doxorubicin HCl liposome injection (DOXIL®) and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR®), tegafur (UFTORAL®), capecitabine (XELODA®), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine, and imatinib (a 2-phenylaminopyrimidine derivative), as well as other c-Kit inhibitors; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK® polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine (ELDISINE®, FILDESIN®); dacarbazine; mannomustine; mitobronitol; mitolactol; pipobroman; gacytosine; arabinoside ("Ara-C"); thiotepa; taxoids, e.g., paclitaxel (TAXOL®), albumin-engineered nanoparticle formulation of paclitaxel (ABRAXANE™), and doxetaxel (TAXOTERE®); chloranbucil; 6-thioguanine; mercaptopurine; methotrexate; platinum analogs such as cisplatin and carboplatin; vinblastine (VELBAN®); platinum; etoposide (VP-16); ifosfamide; mitoxantrone; vincristine (ONCOVIN®); oxaliplatin; leucovovin; vinorelbine (NAVELBINE®); novantrone; edatrexate; daunomycin; aminopterin; ibandronate; topoisomerase inhibitor RFS 2000; difluorometlhylornithine (DMFO); retinoids such as retinoic acid; pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Also included in this definition are anti-hormonal agents that act to regulate, reduce, block, or inhibit the effects of hormones that can promote the growth of cancer, and are often in the form of systemic, or whole-body treatment. They may be hormones themselves. Examples include anti-estrogens and selective estrogen receptor modulators (SERMs), including, for example, tamoxifen (including NOLVADEX® tamoxifen), raloxifene (EVISTA®), droloxifene, 4-hydroxytamoxifen, trioxifene, keoxifene, LY117018, onapristone, and toremifene (FARESTON®); anti-progesterones; estrogen receptor down-regulators (ERDs); estrogen receptor antagonists such as fulvestrant (FASLODEX®); agents that function to suppress or shut down the ovaries, for example, leutinizing hormone-releasing hormone (LHRH) agonists such as leuprolide acetate (LUPRON® and ELIGARD®), goserelin acetate, buserelin acetate and tripterelin; anti-androgens such as flutamide, nilutamide and bicalutamide; and aromatase inhibitors that inhibit the enzyme aromatase, which regulates estrogen production in the adrenal glands, such as, for example, 4(5)-imidazoles, aminoglutethimide, megestrol acetate (MEGASE®), exemestane (AROMASIN®), formestanie, fadrozole, vorozole (RIVISOR®), letrozole (FEMARA®), and anastrozole (ARIMIDEX®). In addition, such definition of chemotherapeutic agents includes bisphosphonates such as clodronate (for example, BONEFOS® or OSTAC®), etidronate (DIDROCAL®), NE-58095, zoledronic acid/zoledronate (ZOMETA®), alendronate (FOSAMAX®), pamidronate (AREDIA®), tiludronate (SKELID®), or risedronate (ACTONEL®); as well as troxacitabine (a 1,3-dioxolane nucleoside cytosine analog); anti-sense oligonucleotides, particularly those that inhibit expression of genes in signaling pathways implicated in abherant cell proliferation, such as, for example, PKC-alpha, Raf, H-Ras, and epidermal growth factor receptor (EGF-R); vaccines such as THERATOPE® vaccine and gene therapy vaccines, for example, ALLOVECTIN® vaccine, LEUVECTIN® vaccine, and VAXID® vaccine; topoisomerase 1 inhibitor (e.g., LURTOTECAN®); an anti-estrogen such as fulvestrant; a Kit inhibitor such as imatinib or EXEL-0862 (a tyrosine kinase inhibitor); EGFR inhibitor such as erlotinib or cetuximab; an anti-VEGF inhibitor such as bevacizumab; irinotecan; rmRH (e.g., ABARELIX®); lapatinib and lapatinib ditosylate (an ErbB-2 and EGFR dual tyrosine kinase small-molecule inhibitor also known as GW572016); 17AAG (geldanamycin derivative that is a heat shock protein (Hsp) 90 poison), and pharmaceutically acceptable salts, acids or derivatives of any of the above.

As used herein, the term "cytokine" refers generically to proteins released by one cell population that act on another cell as intercellular mediators or have an autocrine effect on the cells producing the proteins. Examples of such cytokines include lymphokines, monokines; interleukins ("ILs") such as IL-1, IL-la, IL-2, IL-3, IL-4, IL-5, IL-6, IL-7, IL-8, IL-9, IL10, IL-11, IL-12, IL-13, IL-15, IL-17A-F, IL-18 to IL-29 (such as IL-23), IL-31, including PROLEUKIN® rIL-2; a tumor-necrosis factor such as TNF-α or TNF-β, TGF-β1-3; and other polypeptide factors including leukemia inhibitory factor ("LIF"), ciliary neurotrophic factor ("CNTF"), CNTF-like cytokine ("CLC"), cardiotrophin ("CT"), and kit ligand ("KL").

As used herein, the term "chemokine" refers to soluble factors (e.g., cytokines) that have the ability to selectively induce chemotaxis and activation of leukocytes. They also trigger processes of angiogenesis, inflammation, wound healing, and tumorigenesis. Example chemokines include IL-8, a human homolog of murine keratinocyte chemoattractant (KC).

As used herein and in the appended claims, the singular forms "a," "or," and "the" include plural referents unless the context clearly dictates otherwise.

Reference to "about" a value or parameter herein includes (and describes) variations that are directed to that value or parameter per se. For example, description referring to "about X" includes description of "X".

The phrase "pharmaceutically acceptable salt" as used herein, refers to pharmaceutically acceptable organic or inorganic salts of a compound of the invention. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate", ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. A pharmaceutically acceptable salt may involve the inclusion of another molecule such as an acetate ion, a succinate ion or other counter ion. The counter ion may be any organic or inorganic moiety that stabilizes the charge on the parent compound. Furthermore, a pharmaceutically acceptable salt may have more than one charged atom in its structure. Instances where multiple charged atoms are part of the pharmaceutically acceptable salt can have multiple counter ions. Hence, a pharmaceutically acceptable salt can have one or more charged atoms and/or one or more counter ion.

If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like.

If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

The phrase "pharmaceutically acceptable" indicates that the substance or composition must be compatible chemically and/or toxicologically, with the other ingredients comprising a formulation, and/or the mammal being treated therewith.

It is understood that aspects and variations of the invention described herein include "consisting" and/or "consisting essentially of" aspects and variations.

III. Methods

The methods of this invention may find use in treating conditions where enhanced immunogenicity is desired such as increasing tumor immunogenicity for the treatment of cancer. A variety of cancers may be treated, or their progression may be delayed.

In some embodiments, the individual has melanoma. The melanoma may be at early stage or at late stage. In some embodiments, the individual has colorectal cancer. The colorectal cancer may be at early stage or at late stage. In some embodiments, the individual has non-small cell lung cancer. The non-small cell lung cancer may be at early stage or at late stage. In some embodiments, the individual has pancreatic cancer. The pancreatic cancer may be at early stage or late state. In some embodiments, the individual has a hematological malignancy. The hematological malignancy may be early stage or late stage. In some embodiments, the individual has ovarian cancer. The ovarian cancer may be at early stage or at late stage. In some embodiments, the individual has breast cancer. The breast cancer may be at early stage or at late stage. In some embodiments, the individual has renal cell carcinoma. The renal cell carcinoma may be at early stage or at late stage.

In some embodiments, the subject treated is a human.

The combination therapy of the invention comprises administration of a PD-1 axis binding antagonist and oxaliplatin, leucovorin and 5-FU. In another aspect the invention provides a combination therapy comprising the administration of a PD-1 axis binding antagonist, a VEGF antagonist and oxaliplatin, leucovorin and 5-FU. The PD-1 axis binding antagonist and the VEGF antagonist may be administered in any suitable manner known in the art. For example, The PD-1 axis binding antagonist and the VEGF antagonist may be administered sequentially (at different times) or concurrently (at the same time).

In some embodiments, the methods of the invention may further comprise administering an additional therapy. The additional therapy may be radiation therapy, surgery (e.g., lumpectomy and a mastectomy), chemotherapy, gene therapy, DNA therapy, viral therapy, RNA therapy, immunotherapy, bone marrow transplantation, nanotherapy, monoclonal antibody therapy, or a combination of the foregoing. The additional therapy may be in the form of adjuvant or neoadjuvant therapy. In some embodiments, the additional therapy is the administration of small molecule enzymatic inhibitor or anti-metastatic agent. In some embodiments, the additional therapy is the administration of side-effect limiting agents (e.g., agents intended to lessen the occurrence and/or severity of side effects of treatment, such as anti-nausea agents, etc.). In some embodiments, the additional therapy is radiation therapy. In some embodiments, the additional therapy is surgery. In some embodiments, the additional therapy is a combination of radiation therapy and surgery. The additional therapy may be one or more of the chemotherapeutic agents described hereabove.

Any of the PD-1 axis binding antagonists and the VEGF antagonists described below may be used in the methods of the invention.

PD-1 Axis Binding Antagonists

Provided herein is a method for treating or delaying progression of cancer in an individual comprising administering to the individual an effective amount of a PD-1 axis binding antagonist in combination with oxaliplatin, leucovorin and 5-FU with or without administration of a VEGF antagonist. For example, a PD-1 axis binding antagonist includes a PD-1 binding antagonist, a PD-L1 binding antagonist and a PD-L2 binding antagonist.

In some embodiments, the PD-1 binding antagonist is a molecule that inhibits the binding of PD-1 to its ligand binding partners. In a specific aspect the PD-1 ligand binding partners are PD-L1 and/or PD-L2. In another embodiment, a PD-L1 binding antagonist is a molecule that inhibits the binding of PD-L1 to its binding partners. In a specific aspect, PD-L1 binding partners are PD-1 and/or B7-1. In another embodiment, the PD-L2 binding antagonist is a molecule that inhibits the binding of PD-L2 to its binding partners. In a specific aspect, a PD-L2 binding partner is PD-1. The antagonist may be an antibody, an antigen binding fragment thereof, an immunoadhesin, a fusion protein, or oligopeptide.

In some embodiments, the PD-1 binding antagonist is selected from the group consisting of MDX-1106, Merck 3475 and CT-011. In some embodiments, the PD-L1 binding antagonist is selected from the group consisting of YW243.55.S70 and MDX-1105. In some embodiments, the PD-L2 binding antagonist is AMP-224. MDX-1105, also known as BMS-936559, is an anti-PD-L1 antibody described in WO2007/005874. Antibody YW243.55.S70

(SEQ ID No. 20) is an anti-PD-L1 described in WO 2010/077634 A1. MDX-1106, also known as MDX-1106-04, ONO-4538 or BMS-936558, is an anti-PD-1 antibody described in WO2006/121168. Merck 3745, also known as MK-3475 or SCH-900475, is an anti-PD-1 antibody described in WO2009/114335. CT-011, also known as hBAT or hBAT-1, is an anti-PD-1 antibody described in WO2009/101611. AMP-224, also known as B7-DCIg, is a PD-L2-Fc fusion soluble receptor described in WO2010/027827 and WO2011/066342.

Examples of anti-PD-L1 antibodies useful for the methods of this invention, and methods for making thereof are described in PCT patent application WO 2010/077634 A1, which are incorporated herein by reference.

In some embodiments, the PD-1 axis binding antagonist is an anti-PD-L1 antibody. In some embodiments, the anti-PD-L1 antibody is capable of inhibiting binding between PD-L1 and PD-1 and/or between PD-L1 and B7-1. In some embodiments, the anti-PD-L1 antibody is a monoclonal antibody. In some embodiments, the anti-PD-L1 antibody is an antibody fragment selected from the group consisting of Fab, Fab'-SH, Fv, scFv, and (Fab')$_2$ fragments. In some embodiments, the anti-PD-L1 antibody is a humanized antibody. In some embodiments, the anti-PD-L1 antibody is a human antibody.

The anti-PD-L1 antibodies useful in this invention, including compositions containing such antibodies, such as those described in WO 2010/077634 A1, may be used in combination with oxaliplatin, leucovorin, 5-FU with or without a VEGF antagonist to treat cancer.

In one embodiment, the anti-PD-L1 antibody contains a heavy chain variable region polypeptide comprising an HVR-H1, HVR-H2 and HVR-H3 sequence, wherein:

```
(a) the HVR-H1 sequence is is
                                (SEQ ID NO: 1)
    GFTFSX₁SWIH;

(b) the HVR-H2 sequence is
                                (SEQ ID NO: 2)
    AWIX₂PYGGSX₃YYADSVKG;

(c) the HVR-H3 sequence is
                                (SEQ ID NO: 3)
    RHWPGGFDY;
``` further wherein: $X_1$ is D or G; $X_2$ is S or L; $X_3$ is T or S.

In one specific aspect, $X_1$ is D; $X_2$ is S and $X_3$ is T. In another aspect, the polypeptide further comprises variable region heavy chain framework sequences juxtaposed between the HVRs according to the formula: (HC-FR1)-(HVR-H1)-(HC-FR2)-(HVR-H2)-(HC-FR3)-(HVR-H3)-(HC-FR4). In yet another aspect, the framework sequences are derived from human consensus framework sequences. In a further aspect, the framework sequences are VH subgroup III consensus framework. In a still further aspect, at least one of the framework sequences is the following:

```
HC-FR1 is
                                (SEQ ID NO: 4)
    EVQLVESGGGLVQPGGSLRLSCAAS

HC-FR2 is
                                (SEQ ID NO: 5)
    WVRQAPGKGLEWV

HC-FR3 is
                                (SEQ ID NO: 6)
    RFTISADTSKNTAYLQMNSLRAEDTAVYYCAR

HC-FR4 is
                                (SEQ ID NO: 7)
    WGQGTLVTVSA.
```

In a still further aspect, the heavy chain polypeptide is further combined with a variable region light chain comprising an HVR-L1, HVR-L2 and HVR-L3, wherein:

```
(a) the HVR-L1 sequence is
                                (SEQ ID NO: 8)
    RASQX₄X₅X₆TX₇X₈A;

(b) the HVR-L2 sequence is
                                (SEQ ID NO: 9)
    SASX₉LX₁₀S,;

(c) the HVR-L3 sequence is
                                (SEQ ID NO: 10)
    QQX₁₁X₁₂X₁₃X₁₄PX₁₅T;
``` further wherein: $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a still further aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In a still further aspect, the light chain further comprises variable region light chain framework sequences juxtaposed between the HVRs according to the formula: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the framework sequences are VL kappa I consensus framework. In a still further aspect, at least one of the framework sequence is the following:

```
LC-FR1 is
                                (SEQ ID NO: 11)
    DIQMTQSPSSLSASVGDRVTITC

LC-FR2 is
                                (SEQ ID NO: 12)
    WYQQKPGKAPKLLIY

LC-FR3 is
                                (SEQ ID NO: 13)
    GVPSRFSGSGSGTDFTLTISSLQPEDFATYYC

LC-FR4 is
                                (SEQ ID NO: 14)
    FGQGTKVEIKR.
```

In another embodiment, provided is an isolated anti-PD-L1 antibody or antigen binding fragment comprising a heavy chain and a light chain variable region sequence, wherein:
(a) the heavy chain comprises and HVR-H1, HVR-H2 and HVR-H3, wherein further:

```
(i) the HVR-H1 sequence is
                                (SEQ ID NO: 1)
    GFTFSX₁SWIH;

(ii) the HVR-H2 sequence is
                                (SEQ ID NO: 2)
    AWIX₂PYGGSX₃YYADSVKG
```

-continued (iii) the HVR-H3 sequence is
(SEQ ID NO: 3)
RHWPGGFDY,
and (b) the light chain comprises and HVR-L1, HVR-L2 and HVR-L3, wherein further:

(i) the HVR-L1 sequence is
(SEQ ID NOs: 8)
RASQX$_4$X$_5$X$_6$TX$_7$X$_8$A (ii) the HVR-L2 sequence is
(SEQ ID NOs: 9)
SASX$_9$LX$_{10}$S;
and (iii) the HVR-L3 sequence is
(SEQ ID NOs: 10)
QQX$_{11}$X$_{12}$X$_{13}$X$_{14}$PX$_{15}$T;

Further wherein: $X_1$ is D or G; $X_2$ is S or L; $X_3$ is T or S; $X_4$ is D or V; $X_5$ is V or I; $X_6$ is S or N; $X_7$ is A or F; $X_8$ is V or L; $X_9$ is F or T; $X_{10}$ is Y or A; $X_{11}$ is Y, G, F, or S; $X_{12}$ is L, Y, F or W; $X_{13}$ is Y, N, A, T, G, F or I; $X_{14}$ is H, V, P, T or I; $X_{15}$ is A, W, R, P or T.

In a specific aspect, $X_1$ is D; $X_2$ is S and $X_3$ is T. In another aspect, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H; $X_{15}$ is A. In yet another aspect, $X_1$ is D; $X_2$ is S and $X_3$ is T, $X_4$ is D; $X_5$ is V; $X_6$ is S; $X_7$ is A; $X_8$ is V; $X_9$ is F; $X_{10}$ is Y; $X_{11}$ is Y; $X_{12}$ is L; $X_{13}$ is Y; $X_{14}$ is H and $X_{15}$ is A.

In a further aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In a still further aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

HC-FR1
(SEQ ID NO: 4)
EVQLVESGGGLVQPGGSLRLSCAAS

HC-FR2
(SEQ ID NO: 5)
WVRQAPGKGLEWV

HC-FR3
(SEQ ID NO: 6)
RFTISADTSKNTAYLQMNSLRAEDTAVYYCAR

HC-FR4
(SEQ ID NO: 7)
WGQGTLVTVSA.

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

LC-FR1
(SEQ ID NO: 11)
DIQMTQSPSSLSASVGDRVTITC

LC-FR2
(SEQ ID NO: 12)
WYQQKPGKAPKLLIY

LC-FR3
(SEQ ID NO: 13)
GVPSRFSGSGSGTDFTLTISSLQPEDFATYYC

LC-FR4
(SEQ ID NO: 14)
FGQGTKVEIKR.

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In yet another embodiment, provided is an anti-PD-L1 antibody comprising a heavy chain and a light chain variable region sequence, wherein:

(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, or (b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYH-PAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a still further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

HC-FR1
(SEQ ID NO: 4)
EVQLVESGGGLVQPGGSLRLSCAAS

```
HC-FR2
                               (SEQ ID NO: 5)
WVRQAPGKGLEWV

HC-FR3
                               (SEQ ID NO: 6)
RFTISADTSKNTAYLQMNSLRAEDTAVYYCAR

HC-FR4
                               (SEQ ID NO: 7)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                              (SEQ ID NO: 11)
DIQMTQSPSSLSASVGDRVTITC

LC-FR2
                              (SEQ ID NO: 12)
WYQQKPGKAPKLLIY

LC-FR3
                              (SEQ ID NO: 13)
GVPSRFSGSGSGTDFTLTISSLQPEDFATYYC

LC-FR4
                              (SEQ ID NO: 14)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, provided is an isolated anti-PD-L1 antibody comprising a heavy chain and a light chain variable region sequence, wherein:

(a) the heavy chain sequence has at least 85% sequence identity to the heavy chain sequence:

```
                                       (SEQ ID NO: 20)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSA,
```
or (b) the light chain sequences has at least 85% sequence identity to the light chain sequence:

```
                                       (SEQ ID NO: 21)
DIQMTQSPSSLSASVGDRVTITCRASQDVSTAVAWYQQKPGKAPKLLIY

SASFLYSGVPSRFSGSGSGTDFTLTISSLQPEDFATYYCQQYLYHPATF

GQGTKVEIKR.
```

In a specific aspect, the sequence identity is 86%, 87%, 88%, 89%, 90%, 91%, 92%, 93%, 94%, 95%, 96%, 97%, 98%, 99% or 100%. In another aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                              (SEQ ID NO: 4)
EVQLVESGGGLVQPGGSLRLSCAAS

HC-FR2
                              (SEQ ID NO: 5)
WVRQAPGKGLEWV

HC-FR3
                              (SEQ ID NO: 6)
RFTISADTSKNTAYLQMNSLRAEDTAVYYCAR

HC-FR4
                              (SEQ ID NO: 7)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                              (SEQ ID NO: 11)
DIQMTQSPSSLSASVGDRVTITC

LC-FR2
                              (SEQ ID NO: 12)
WYQQKPGKAPKLLIY

LC-FR3
                              (SEQ ID NO: 13)
GVPSRFSGSGSGTDFTLTISSLQPEDFATYYC

LC-FR4
                              (SEQ ID NO: 14)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further embodiment, the effector-less Fc mutation is an N297A or D265A/N297A substitution in the constant region.

In a still further embodiment, the invention provides for compositions comprising any of the above described anti-PD-L1 antibodies in combination with at least one pharmaceutically-acceptable carrier.

In a still further embodiment, provided is an isolated nucleic acid encoding a light chain or a heavy chain variable region sequence of an anti-PD-L1 antibody, wherein:
(a) the heavy chain further comprises and HVR-H1, HVR-H2 and an HVR-H3 sequence having at least 85% sequence identity to GFTFSDSWIH (SEQ ID NO:15), AWISPYGGSTYYADSVKG (SEQ ID NO:16) and RHWPGGFDY (SEQ ID NO:3), respectively, and
(b) the light chain further comprises an HVR-L1, HVR-L2 and an HVR-L3 sequence having at least 85% sequence identity to RASQDVSTAVA (SEQ ID NO:17), SASFLYS (SEQ ID NO:18) and QQYLYHPAT (SEQ ID NO:19), respectively.

In a specific aspect, the sequence identity is 86%, 87%, 88%, 89%, 90%, 91%, 92%, 93%, 94%, 95%, 96%, 97%, 98%, 99% or 100%. In aspect, the heavy chain variable region comprises one or more framework sequences juxtaposed between the HVRs as: (HC-FR1)-(HVR-H1)-(HC-FR2)-(HVR-H2)-(HC-FR3)-(HVR-H3)-(HC-FR4), and the light chain variable regions comprises one or more framework sequences juxtaposed between the HVRs as: (LC-FR1)-(HVR-L1)-(LC-FR2)-(HVR-L2)-(LC-FR3)-(HVR-L3)-(LC-FR4). In yet another aspect, the framework sequences are derived from human consensus framework sequences. In a further aspect, the heavy chain framework sequences are derived from a Kabat subgroup I, II, or III sequence. In a still further aspect, the heavy chain framework sequence is a VH subgroup III consensus framework. In a still further aspect, one or more of the heavy chain framework sequences is the following:

```
HC-FR1
                                          (SEQ ID NO: 4)
EVQLVESGGGLVQPGGSLRLSCAAS

HC-FR2
                                          (SEQ ID NO: 5)
WVRQAPGKGLEWV

HC-FR3
                                          (SEQ ID NO: 6)
RFTISADTSKNTAYLQMNSLRAEDTAVYYCAR

HC-FR4
                                          (SEQ ID NO: 7)
WGQGTLVTVSA.
```

In a still further aspect, the light chain framework sequences are derived from a Kabat kappa I, II, II or IV subgroup sequence. In a still further aspect, the light chain framework sequences are VL kappa I consensus framework. In a still further aspect, one or more of the light chain framework sequences is the following:

```
LC-FR1
                                          (SEQ ID NO: 11)
DIQMTQSPSSLSASVGDRVTITC

LC-FR2
                                          (SEQ ID NO: 12)
WYQQKPGKAPKLLIY

LC-FR3
                                          (SEQ ID NO: 13)
GVPSRFSGSGSGTDFTLTISSLQPEDFATYYC

LC-FR4
                                          (SEQ ID NO: 14)
FGQGTKVEIKR.
```

In a still further specific aspect, the antibody further comprises a human or murine constant region. In a still further aspect, the human constant region is selected from the group consisting of IgG1, IgG2, IgG2, IgG3, IgG4. In a still further specific aspect, the human constant region is IgG1. In a still further aspect, the murine constant region is selected from the group consisting of IgG1, IgG2A, IgG2B, IgG3. In a still further aspect, the murine constant region if IgG2A. In a still further specific aspect, the antibody has reduced or minimal effector function. In a still further specific aspect, the minimal effector function results from production in prokaryotic cells. In a still further specific aspect the minimal effector function results from an "effector-less Fc mutation" or aglycosylation. In still a further aspect, the effector-less Fc mutation is an N297A or D265A/N297A substitution in the constant region.

In a still further aspect, the nucleic acid further comprises a vector suitable for expression of the nucleic acid encoding any of the previously described anti-PD-L1 antibodies. In a still further specific aspect, the vector further comprises a host cell suitable for expression of the nucleic acid. In a still further specific aspect, the host cell is a eukaryotic cell or a prokaryotic cell. In a still further specific aspect, the eukaryotic cell is a mammalian cell, such as Chinese Hamster Ovary (CHO).

The anti-PD-L1 antibody or antigen binding fragment thereof, may be made using methods known in the art, for example, by a process comprising culturing a host cell containing nucleic acid encoding any of the previously described anti-PD-L1 antibodies or antigen-binding fragment in a form suitable for expression, under conditions suitable to produce such antibody or fragment, and recovering the antibody or fragment.

In a still further embodiment, the invention provides for a composition comprising an anti-PD-L1 antibody or antigen binding fragment thereof as provided herein and at least one pharmaceutically acceptable carrier.

VEGF Antagonists

The invention provides methods for treating cancer or slowing progression of cancer in an individual comprising administering an effective amount of a PD-1 pathway antagonist and a VEGF antagonist in combination with oxaliplatin, leucovorin and 5-FU. Any known VEGF antagonists are intended.

(i) VEGF Antigen

The VEGF antigen to be used for production of antibodies may be, e.g., the VEGF$_{165}$ molecule as well as other isoforms of VEGF or a fragment thereof containing the desired epitope. Other forms of VEGF useful for generating anti-VEGF antibodies of the invention will be apparent to those skilled in the art.

Human VEGF was obtained by first screening a cDNA library prepared from human cells, using bovine VEGF cDNA as a hybridization probe. Leung et al. (1989) *Science*, 246:1306. One cDNA identified thereby encodes a 165-amino acid protein having greater than 95% homology to bovine VEGF; this 165-amino acid protein is typically referred to as human VEGF (hVEGF) or VEGF$_{165}$. The mitogenic activity of human VEGF was confirmed by expressing the human VEGF cDNA in mammalian host cells. Media conditioned by cells transfected with the human VEGF cDNA promoted the proliferation of capillary endothelial cells, whereas control cells did not. Leung et al. (1989) *Science*, supra.

Although a vascular endothelial cell growth factor could be isolated and purified from natural sources for subsequent therapeutic use, the relatively low concentrations of the protein in follicular cells and the high cost, both in terms of effort and expense, of recovering VEGF proved commercially unavailing. Accordingly, further efforts were undertaken to clone and express VEGF via recombinant DNA techniques. (See, e.g., Ferrara, *Laboratory Investigation* 72:615-618 (1995), and the references cited therein).

VEGF is expressed in a variety of tissues as multiple homodimeric forms (121, 145, 165, 189, and 206 amino acids per monomer) resulting from alternative RNA splicing. $VEGF_{121}$ is a soluble mitogen that does not bind heparin; the longer forms of VEGF bind heparin with progressively higher affinity. The heparin-binding forms of VEGF can be cleaved in the carboxy terminus by plasmin to release a diffusible form(s) of VEGF. Amino acid sequencing of the carboxy terminal peptide identified after plasmin cleavage is $Arg_{110}$-$Ala_{111}$. Amino terminal "core" protein, VEGF (1-110) isolated as a homodimer, binds neutralizing monoclonal antibodies (such as the antibodies referred to as 4.6.1 and 3.2E3.1.1) and soluble forms of VEGF receptors with similar affinity compared to the intact $VEGF_{165}$ homodimer.

Several molecules structurally related to VEGF have also been identified, including placenta growth factor (PlGF), VEGF-B, VEGF-C, VEGF-D and VEGF-E. Ferrara and Davis-Smyth (1987) Endocr. Rev., supra; Ogawa et al. *J. Biological Chem.* 273:31273-31281(1998); Meyer et al. *EMBO J.*, 18:363-374(1999). A receptor tyrosine kinase, Flt-4 (VEGFR-3), has been identified as the receptor for VEGF-C and VEGF-D. Joukov et al. *EMBO. J.* 15:1751 (1996); Lee et al. *Proc. Natl. Acad. Sci. USA* 93:1988-1992 (1996); Achen et al. (1998) *Proc. Natl. Acad. Sci. USA* 95:548-553. VEGF-C has been shown to be involved in the regulation of lymphatic angiogenesis. Jeltsch et al. *Science* 276:1423-1425(1997).

Two VEGF receptors have been identified, Flt-1 (also called VEGFR-1) and KDR (also called VEGFR-2). Shibuya et al. (1990) *Oncogene* 8:519-527; de Vries et al. (1992) *Science* 255:989-991; Terman et al. (1992) *Biochem. Biophys. Res. Commun.* 187:1579-1586. Neuropilin-1 has been shown to be a selective VEGF receptor, able to bind the heparin-binding VEGF isoforms (Soker et al. (1998) *Cell* 92:735-45). Both Flt-I and KDR belong to the family of receptor tyrosine kinases (RTKs). The RTKs comprise a large family of transmembrane receptors with diverse biological activities. At present, at least nineteen (19) distinct RTK subfamilies have been identified. The receptor tyrosine kinase (RTK) family includes receptors that are crucial for the growth and differentiation of a variety of cell types (Yarden and Ullrich (1988) *Ann. Rev. Biochem.* 57:433-478; Ullrich and Schlessinger (1990) *Cell* 61:243-254). The intrinsic function of RTKs is activated upon ligand binding, which results in phosphorylation of the receptor and multiple cellular substrates, and subsequently in a variety of cellular responses (Ullrich & Schlessinger (1990) *Cell* 61:203-212). Thus, receptor tyrosine kinase mediated signal transduction is initiated by extracellular interaction with a specific growth factor (ligand), typically followed by receptor dimerization, stimulation of the intrinsic protein tyrosine kinase activity and receptor trans-phosphorylation. Binding sites are thereby created for intracellular signal transduction molecules and lead to the formation of complexes with a spectrum of cytoplasmic signaling molecules that facilitate the appropriate cellular response. (e.g., cell division, differentiation, metabolic effects, changes in the extracellular microenvironment) see, Schlessinger and Ullrich (1992) *Neuron* 9:1-20. Structurally, both Flt-1 and KDR have seven immunoglobulin-like domains in the extracellular domain, a single transmembrane region, and a consensus tyrosine kinase sequence which is interrupted by a kinase-insert domain. Matthews et al. (1991) *Proc. Natl. Acad. Sci. USA* 88:9026-9030; Terman et al. (1991) *Oncogene* 6:1677-1683.

(ii) Anti-VEGF Antibodies

Anti-VEGF antibodies that are useful in the methods of the invention include any antibody, or antigen binding fragment thereof, that bind with sufficient affinity and specificity to VEGF and can reduce or inhibit the biological activity of VEGF. An anti-VEGF antibody will usually not bind to other VEGF homologues such as VEGF-B or VEGF-C, nor other growth factors such as PlGF, PDGF, or bFGF.

In certain embodiments of the invention, the anti-VEGF antibodies include, but are not limited to, a monoclonal antibody that binds to the same epitope as the monoclonal anti-VEGF antibody A4.6.1 produced by hybridoma ATCC HB 10709; a recombinant humanized anti-VEGF monoclonal antibody generated according to Presta et al. (1997) *Cancer Res.* 57:4593-4599. In one embodiment, the anti-VEGF antibody is "Bevacizumab (BV)", also known as "rhuMAb VEGF" or "AVASTIN®". It comprises mutated human IgG1 framework regions and antigen-binding complementarity-determining regions from the murine anti-hVEGF monoclonal antibody A.4.6.1 that blocks binding of human VEGF to its receptors. Approximately 93% of the amino acid sequence of bevacizumab, including most of the framework regions, is derived from human IgG1, and about 7% of the sequence is derived from the murine antibody A4.6.1.

Bevacizumab and other humanized anti-VEGF antibodies are further described in U.S. Pat. No. 6,884,879 issued Feb. 26, 2005. Additional antibodies include the G6 or B20 series antibodies (e.g., G6-31, B20-4.1), as described in PCT Publication No. WO2005/012359, PCT Publication No. WO2005/044853, and U.S. Patent Application 60/991,302, the content of these patent applications are expressly incorporated herein by reference. For additional antibodies see U.S. Pat. Nos. 7,060,269, 6,582,959, 6,703,020; 6,054,297; WO98/45332; WO 96/30046; WO94/10202; EP 0666868B1; U.S. Patent Application Publication Nos. 2006009360, 20050186208, 20030206899, 20030190317, 20030203409, and 20050112126; and Popkov et al., Journal of Immunological Methods 288:149-164 (2004). Other antibodies include those that bind to a functional epitope on human VEGF comprising of residues F17, M18, D19, Y21, Y25, Q89, I91, K101, E103, and C104 or, alternatively, comprising residues F17, Y21, Q22, Y25, D63, I83 and Q89.

In one embodiment of the invention, the anti-VEGF antibody comprises a heavy chain variable region comprising the following amino acid sequence:

(SEQ ID NO: 22)
EVQLVESGGG LVQPGGSLRL SCAASGYTFT NYGMNWVRQA

PGKGLEWVGW INTYTGEPTY AADFKRRFTF SLDTSKSTAY

LQMNSLRAED TAVYYCAKYP HYYGSSHWYF DVWGQGTLVT VSS.

and a light chain variable region comprising the following amino acid sequence:

```
                                      (SEQ ID NO: 23)
DIQMTQSPSS LSASVGDRVT ITCSASQDIS NYLNWYQQKP

GKAPKVLIYF TSSLHSGVPS RFSGSGSGTD FTLTISSLQP

EDFATYYCQQ YSTVPWTFGQ GTKVEIKR.
```

In some embodiments the anti-VEGF antibody comprises a CDRH1 comprising the following amino acid sequence: GYTFTNYGMN (SEQ ID NO:24), a CDRH2 comprising the following amino acid sequence: WINTYTGEPTYAADFKR (SEQ ID NO:25), a CDRH3 comprising the following amino acid sequence: YPHYYGSSHWYFDV (SEQ ID NO:26), a CDRL1 comprising the following amino acid sequence: SASQDISNYLN (SEQ ID NO:27), a CDRL2 comprising the following amino acid sequence: FTSSLHS (SEQ ID NO:28) and a CDRL3 comprising the amino acid sequence: QQYSTVPWT (SEQ ID NO:29).

A "G6 series antibody" according to this invention, is an anti-VEGF antibody that is derived from a sequence of a G6 antibody or G6-derived antibody according to any one of FIGS. 7, 24-26, and 34-35 of PCT Publication No. WO2005/012359, the entire disclosure of which is expressly incorporated herein by reference. See also PCT Publication No. WO2005/044853, the entire disclosure of which is expressly incorporated herein by reference. In one embodiment, the G6 series antibody binds to a functional epitope on human VEGF comprising residues F17, Y21, Q22, Y25, D63, I83 and Q89.

A "B20 series antibody" according to this invention is an anti-VEGF antibody that is derived from a sequence of the B20 antibody or a B20-derived antibody according to any one of FIGS. 27-29 of PCT Publication No. WO2005/012359, the entire disclosure of which is expressly incorporated herein by reference. See also PCT Publication No. WO2005/044853, and U.S. Patent Application 60/991,302, the content of these patent applications are expressly incorporated herein by reference. In one embodiment, the B20 series antibody binds to a functional epitope on human VEGF comprising residues F17, M18, D19, Y21, Y25, Q89, I91, K101, E103, and C104.

A "functional epitope" according to this invention refers to amino acid residues of an antigen that contribute energetically to the binding of an antibody. Mutation of any one of the energetically contributing residues of the antigen (for example, mutation of wild-type VEGF by alanine or homolog mutation) will disrupt the binding of the antibody such that the relative affinity ratio (IC50mutant VEGF/IC50wild-type VEGF) of the antibody will be greater than 5 (see Example 2 of WO2005/012359). In one embodiment, the relative affinity ratio is determined by a solution binding phage displaying ELISA. Briefly, 96-well Maxisorp immunoplates (NUNC) are coated overnight at 4° C. with an Fab form of the antibody to be tested at a concentration of 2 ug/ml in PBS, and blocked with PBS, 0.5% BSA, and 0.05% Tween20 (PBT) for 2 h at room temperature. Serial dilutions of phage displaying hVEGF alanine point mutants (residues 8-109 form) or wild type hVEGF (8-109) in PBT are first incubated on the Fab-coated plates for 15 min at room temperature, and the plates are washed with PBS, 0.05% Tween20 (PBST). The bound phage is detected with an anti-M13 monoclonal antibody horseradish peroxidase (Amersham Pharmacia) conjugate diluted 1:5000 in PBT, developed with 3,3',5,5'-tetramethylbenzidine (TMB, Kirkegaard & Perry Labs, Gaithersburg, Md.) substrate for approximately 5 min, quenched with 1.0 M H3PO4, and read spectrophotometrically at 450 nm. The ratio of IC50 values (IC50,ala/IC50,wt) represents the fold of reduction in binding affinity (the relative binding affinity).

(iii) VEGF Receptor Molecules

The two best characterized VEGF receptors are VEGFR1 (also known as Flt-1) and VEGFR2 (also known as KDR and FLK-1 for the murine homolog). The specificity of each receptor for each VEGF family member varies but VEGF-A binds to both Flt-1 and KDR. The full length Flt-1 receptor includes an extracellular domain that has seven Ig domains, a transmembrane domain, and an intracellular domain with tyrosine kinase activity. The extracellular domain is involved in the binding of VEGF and the intracellular domain is involved in signal transduction.

VEGF receptor molecules, or fragments thereof, that specifically bind to VEGF can be used in the methods of the invention to bind to and sequester the VEGF protein, thereby preventing it from signaling. In certain embodiments, the VEGF receptor molecule, or VEGF binding fragment thereof, is a soluble form, such as sFlt-1. A soluble form of the receptor exerts an inhibitory effect on the biological activity of the VEGF protein by binding to VEGF, thereby preventing it from binding to its natural receptors present on the surface of target cells. Also included are VEGF receptor fusion proteins, examples of which are described below.

A chimeric VEGF receptor protein is a receptor molecule having amino acid sequences derived from at least two different proteins, at least one of which is a VEGF receptor protein (e.g., the flt-1 or KDR receptor), that is capable of binding to and inhibiting the biological activity of VEGF. In certain embodiments, the chimeric VEGF receptor proteins of the invention consist of amino acid sequences derived from only two different VEGF receptor molecules; however, amino acid sequences comprising one, two, three, four, five, six, or all seven Ig-like domains from the extracellular ligand-binding region of the flt-1 and/or KDR receptor can be linked to amino acid sequences from other unrelated proteins, for example, immunoglobulin sequences. Other amino acid sequences to which Ig-like domains are combined will be readily apparent to those of ordinary skill in the art. Examples of chimeric VEGF receptor proteins include, e.g., soluble Flt-1/Fc, KDR/Fc, or FLt-1/KDR/Fc (also known as VEGF Trap). (See for example PCT Application Publication No. WO97/44453)

A soluble VEGF receptor protein or chimeric VEGF receptor proteins of the invention includes VEGF receptor proteins which are not fixed to the surface of cells via a transmembrane domain. As such, soluble forms of the VEGF receptor, including chimeric receptor proteins, while capable of binding to and inactivating VEGF, do not comprise a transmembrane domain and thus generally do not become associated with the cell membrane of cells in which the molecule is expressed.

IV. Kits

In another aspect, provided is a kit comprising a PD-L1 axis binding antagonist and/or a VEGF antagonist for treating or delaying progression of a cancer in an individual or for enhancing immune function of an individual having cancer. In some embodiments, the kit comprises a PD-1 axis binding antagonist and a package insert comprising instructions for using the PD-1 axis binding antagonist in combination with oxaliplatin, leucovorin, 5-FU with or without a VEGF antagonist to treat or delay progression of cancer in an individual or to enhance immune function of an individual having cancer. In some embodiments, the kit comprises oxaliplatin, leucovorin, 5-FU with or without a VEGF antagonist and a package insert comprising instructions for using the oxaliplatin, leucovorin, 5-FU with or without a VEGF antagonist in combination with a PD-1 axis binding antagonist to treat or delay progression of cancer in an individual or to enhance immune function of an individual having cancer. In some embodiments, the kit comprises a PD-1axis binding antagonist and oxaliplatin, leucovorin, 5-FU with or without a VEGF antagonist, and a package insert comprising instructions for using the PD-1 axis binding antagonist and the oxaliplatin, leucovorin, 5-FU with or without a VEGF antagonist to treat or delay progression of cancer in an individual or to enhance immune function of an individual having cancer. Any of the PD-1 axis binding antagonists and/or VEGF antagonists described herein may be included in the kits.

EXAMPLES

The invention can be further understood by reference to the following examples, which are provided by way of illustration and are not meant to be limiting.

Example 1: FOLFOX with or without Anti-VEGF Antibody Enhanced Anti-Tumor Activity of Anti-PD-L1

To determine if FOLFOX (oxaliplatin, leucovorin and 5-fluorouracil) with or without anti-VEGF antibody enhanced the anti-tumor activity of anti-PD-L1 mouse models of colorectal cancer were treated with the combination treatments. Briefly, female C57BL/6 mice were inoculated subcutaneously in the unilateral thoracic region with 100,000 MC38 murine colorectal cells in 100 microliters of HBSS:matrigel. When mice achieved a mean tumor volume of 220 mm$^3$, they were randomly assigned to one of the treatment groups outlined below, at experimental day 0. Treatment was initiated on experimental day 1. Mice were weighed and tumors were measured 2-3 times per week for the duration of the study.
Experimental Groups:
1) Control (isotype control antibody (anti-gp120 antibody)), 10 mg/kg ip, 100 microliters, administered three times a week for three weeks, n=10
2) anti-PD-L1 antibody, 10 mg/kg ip, 100 microliters, administered three times a week for three weeks, n=10
3) FOLFOX (see below), administered once a week for two weeks, n=10
4) FOLFOX (see below), administered once a week for two weeks+anti-PD-L1 antibody, 10 mg/kg ip, 100 microliters, administered three times a week for three weeks, n=10
5) FOLFOX (see below), administered once a week for two weeks+anti-VEGF antibody, 5 mg/kg ip, 100 microliters, administered two times a week for three weeks, n=10
6) FOLFOX (see below), administered once a week for two weeks+anti-VEGF antibody, 5 mg/kg ip, 100 uL, administered two times a week for three weeks+anti-PD-L1 antibody, 10 mg/kg ip, 100 microliters, administered three times a week for three weeks, n=10
ip=intraperitoneally
sc=subcutaneously
For these studies, FOLFOX dosing was carried out as follows: on experimental day 1 and experimental day 8, mice were administered oxaliplatin, 5 mg/kg ip in 50 microliters of water immediately followed by leucovorin, 100 mg/kg ip in 250 microliters of water (administered at time=0 hour) and 5-FU, 25 mg/kg ip immediately followed by 5-FU, 25 mg/kg sc (administered at time=2 hour). Anti-PD-L1 antibody and anti-gp120 antibody were dosed on experimental days 1, 3, 5, 8, 10, 12, 15, 17, and 19 (administered at time=4 hours). Anti-VEGF antibody was dosed on experimental day 1, 4, 8, 11, 15, 18 (administered at time=6 hours).

Mice were monitored for tumor growth and body weight changes. Tumor volumes were measured using UltraCal-IV calipers (Model 54-10-111; Fred V. Fowler Company; Newton, Mass.). The following formula was used to calculate tumor volume:

Tumor Volume (mm$^3$)=(Length×Width$^2$)×0.5

Length and width measurements were perpendicular to one another. Animal body weights were measured using an Adventura Pro AV812 scale (Ohaus Corporation; Pine Brook, N.J.). Percent body weight change was calculated using the following formula:

Body weight change (%)=[(Weight$_{Day\ new}$−Weight$_{Day}$)/Weight$_{Day\ 0}$]×100

Data were analyzed using R, version 2.9.2 (R Development Core Team 2008; R Foundation for Statistical Computing; Vienna, Austria), and the mixed models were fit within R using the nlme package, version 3.1-96 (Pinheiro et al. 2009). Plotting was performed in Prism, version 5.0b for Mac (GraphPad Software, Inc.; La Jolla, Calif.).

A mixed modeling approach was used to analyze the repeated measurement of tumor volumes from the same animals over time (Pinheiro and Bates 2000). This approach addresses both repeated measurements and modest dropouts before study end for reasons classifiable statistically as missing at random (MAR). The fixed effect changes in log$_2$(volume) by time and dose are modeled as the sum of the main effects and interaction of a natural cubic regression spline basis in time with an auto-determined natural spline basis in dose. Intercepts and growth rates (slopes) were assumed to vary randomly by animal. Tumor growth inhibition as a percentage of the control-treated group (% TGI) was calculated as the percentage of the area under the fitted curve (AUC) for the respective treatment group per day in relation to the control while the control treated mice were still on study, using the following formula:

% TGI=100×(1−AUC$_{dose}$/AUC$_{vehicles}$)

For these studies, Complete Response (CR) was defined as an individual animal whose tumor volume fell below the Limit of Detection (LOD), at any time during the study. Partial Response (PR) was defined as an individual animal whose tumor volume decreased by 50% of its initial tumor volume at any time during the study. Overall Response Rate (ORR) was defined as the sum of the complete and partial responses. Time To Progression 5× (TTP5×) was defined as the time in days for a group's fitted tumor volume (based upon the mixed modeling analysis described above) to exceed 5 times the starting volume, rounded to the nearest half day and reported as the TTP5× for that group. Linear mixed-effects analysis was also employed to analyze the repeated measurement of body weight changes from the same animals over time.

Figure 4:
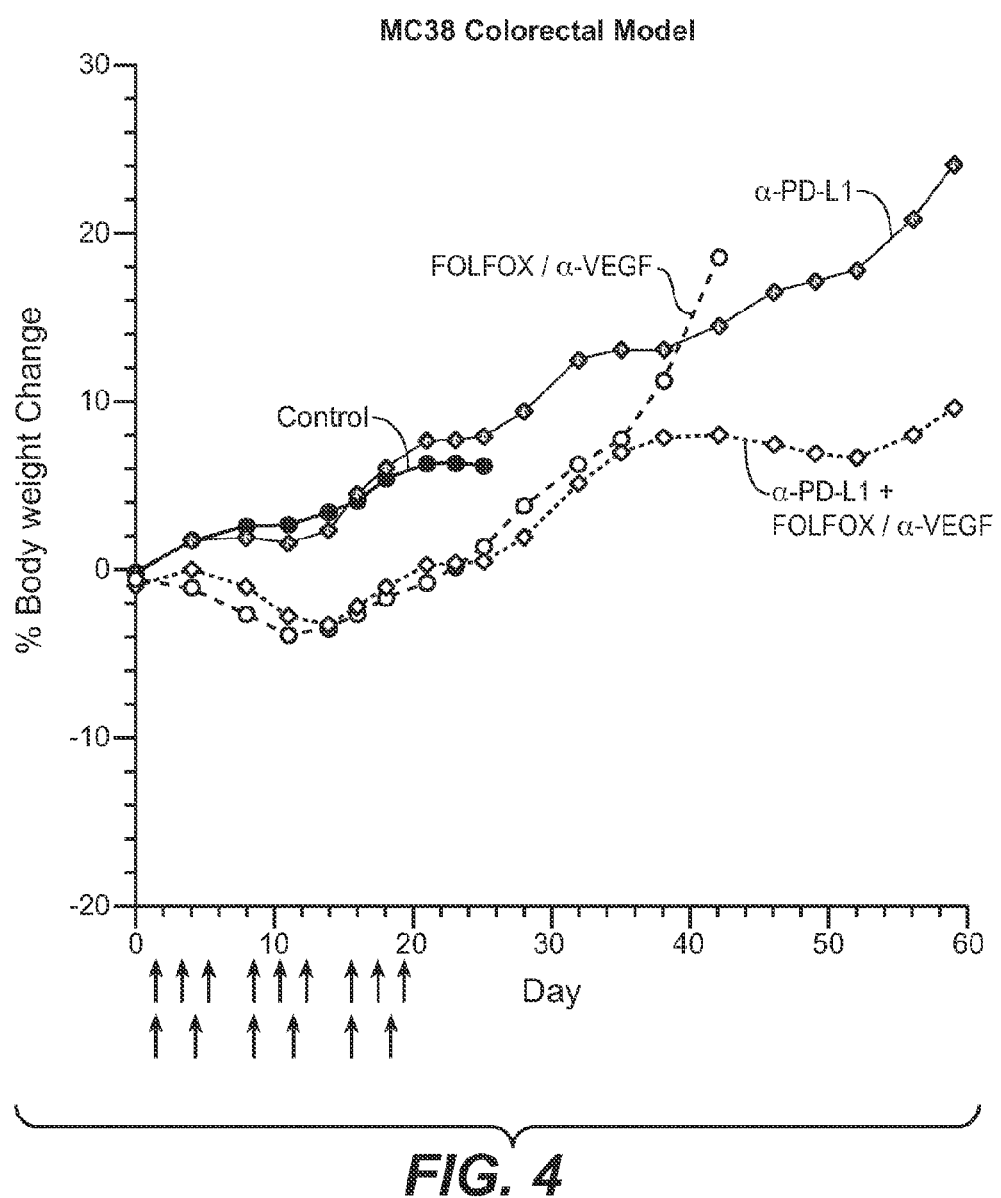
FIG. 4 is a graph showing changes in body weight for the treatment groups shown in FIG. 3.

Blockade of the PD-1 axis using anti-PD-L1 antibody was effective as a single agent therapy at preventing tumor growth. Combination treatment of anti-PD-L1 antibodies with oxaliplatin, leucovorin and 5-FU (FOLFOX) significantly inhibited tumor growth indicating that this chemotherapy combination enhanced the anti-tumor activity of anti-PD-L1 antibodies (FIG. 1). Addition of anti-VEGF to this combination treatment further enhanced this anti-tumor activity and as well as the durability of the anti-tumor response even after the cessation of treatment (FIG. 4).

Example 2: A Phase 1b Study of MPDL3280A with Bevacizumab with or without Modified FOLFOX-6

The primary aim of the study is to assess the safety, pharmacology and preliminary efficacy of MPDL3280A administered with bevacizumab (Arm A) and with bevacizumab plus FOLFOX (specifically, modified FOLFOX-6, or mFOLFOX-6; Arm B) in patients with solid tumors including metastatic colorectal cancer (mCRC). Arm A will evaluate MPDL3280A at 10 mg/kg (or a selected dose level not to exceed the single-agent MTD or MAD) with bevacizumab (15 mg/kg) on an every-3-week (q3w) schedule for up to one year. Patients who have not received oxaliplatin for metastatic disease will be enrolled in Arm B to receive MPDL3280A with bevacizumab and FOLFOX on an every-2-week (q2w) schedule. mFOLFOX-6 regimen consist of the following: oxaliplatin (85 mg/m$^2$) administered intravenously (IV) concurrently with leucovorin (400 mg/m$^2$) administered IV over about 120 minutes followed by 5-FU (400 mg/m2) administered as an IV bolus, followed by 2400 mg/m$^2$ administered by continuous IV infusion over about 46 hours. Oxaliplatin will be administered for up to eight cycles. Treatment may be continued for up to one year.

What is claimed is:

1. A method for treating or delaying progression of colorectal cancer in an individual comprising administering to the individual an effective amount of an anti-PD-L1 antibody, oxaliplatin, leucovorin and 5-FU, wherein the method further comprises administering bevacizumab, wherein the anti-PD-L1 antibody comprises a heavy chain variable region and a light chain variable region, wherein:
   (a) the heavy chain variable region comprises an HVR-H1, HVR-H2 and HVR-H3, and wherein:
      (i) the HVR-H1 comprises the amino acid sequence of SEQ ID NO: 15;
      (ii) the HVR-H2 comprises the amino acid sequence of SEQ ID NO: 16;
      (iii) the HVR-H3 comprises the amino acid sequence of SEQ ID NO: 3; and
   (b) the light chain variable region comprises an HVR-L1, HVR-L2 and HVR-L3, and wherein:
      (iv) the HVR-L1 comprises the amino acid sequence of SEQ ID NO: 17;
      (v) the HVR-L2 comprises the amino acid sequence of SEQ ID NO: 18; and
      (vi) the HVR-L3 comprises the amino acid sequence of SEQ ID NO: 19.

2. The method of claim 1, wherein the anti-PD-L1 antibody is a monoclonal antibody.

3. The method of claim 1, wherein the anti-PD-L1 antibody is an antibody fragment selected from the group consisting of Fab, Fab'-SH, Fv, scFv, and (Fab')$_2$ fragments.

4. The method of claim 1, wherein the anti-PD-L1 antibody is a humanized antibody.

5. The method of claim 1, wherein the anti-PD-L1 antibody comprises a heavy chain variable region and a light chain variable region, wherein:
   (a) the heavy chain variable region amino acid sequence has at least 90% sequence identity to the heavy chain variable region amino acid sequence of SEQ ID NO:20, and
   (b) the light chain variable region amino acid sequence has at least 90% sequence identity to the light chain variable region amino acid sequence of SEQ ID NO:21.

6. The method of claim 5, wherein:
   (a) the heavy chain variable region amino acid sequence has at least 95% sequence identity to the heavy chain variable region amino acid sequence of SEQ ID NO:20, and
   (b) the light chain variable region amino acid sequence has at least 95% sequence identity to the light chain variable region amino acid sequence of SEQ ID NO:21.

7. The method of claim 6, wherein:
   (a) the heavy chain variable region amino acid sequence has at least 99% sequence identity to the heavy chain variable region amino acid sequence of SEQ ID NO:20, and
   (b) the light chain variable region amino acid sequence has at least 99% sequence identity to the light chain variable region amino acid sequence of SEQ ID NO:21.

8. The method of claim 7, wherein
(a) the heavy chain variable region amino acid sequence has at least 99% sequence identity to the heavy chain variable region amino acid sequence of SEQ ID NO:20, and
(b) the light chain variable region comprises the amino acid sequence of SEQ ID NO:21.

9. The method of claim 8, wherein the anti-PD-L1 antibody further comprises a human IgG1 constant region.

10. The method of claim 9, wherein the anti-PD-L1 antibody comprises an effector-less Fc mutation, wherein the effector-less Fc mutation is N297A.

* * * * *

```
                        SEQUENCE LISTING

<160> NUMBER OF SEQ ID NOS: 37

<210> SEQ ID NO 1
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (6)..(6)
<223> OTHER INFORMATION: Asp or Gly
<220> FEATURE:
<223> OTHER INFORMATION: see specification as filed for detailed
      description of substitutions and preferred embodiments

<400> SEQUENCE: 1

Gly Phe Thr Phe Ser Xaa Ser Trp Ile His
1               5                   10

<210> SEQ ID NO 2
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Ser or Leu
<220> FEATURE:
<221> NAME/KEY: MOD_RES
<222> LOCATION: (10)..(10)
<223> OTHER INFORMATION: Thr or Ser
<220> FEATURE:
<223> OTHER INFORMATION: see specification as filed for detailed
      description of substitutions and preferred embodiments

<400> SEQUENCE: 2

Ala Trp Ile Xaa Pro Tyr Gly Gly Ser Xaa Tyr Tyr Ala Asp Ser Val
1               5                   10                  15

Lys Gly

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
```

```
<400> SEQUENCE: 3

Arg His Trp Pro Gly Gly Phe Asp Tyr
1               5

<210> SEQ ID NO 4
<211> LENGTH: 25
<212> TYPE: PRT
<213> ORGANISM: Homo sapiens

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 5
<211> LENGTH: 13
<212> TYPE: PRT
<213> ORGANISM: Homo sapiens

<400> SEQUENCE: 5

Trp Val Arg Gln Ala Pro Gly Lys Gly Leu Glu Trp Val
1               5                   10

<210> SEQ ID NO 6
<211> LENGTH: 32
<212> TYPE: PRT
<213> ORGANISM: Homo sapiens

<400> SEQUENCE: 6

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 7
<211> LENGTH: 11
<212> TYPE: PRT
<213> ORGANISM: Homo sapiens

<400> SEQUENCE: 7

Trp Gly Gln Gly Thr Leu Val Thr Val Ser Ala
1               5                   10

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (5)..(5)
<223> OTHER INFORMATION: Asp or Val
<220> FEATURE:
<221> NAME/KEY: MOD_RES
<222> LOCATION: (6)..(6)
<223> OTHER INFORMATION: Val or Ile
<220> FEATURE:
<221> NAME/KEY: MOD_RES
<222> LOCATION: (7)..(7)
<223> OTHER INFORMATION: Ser or Asn
<220> FEATURE:
<221> NAME/KEY: MOD_RES
<222> LOCATION: (9)..(9)
<223> OTHER INFORMATION: Ala or Phe
```

-continued

```
<220> FEATURE:
<221> NAME/KEY: MOD_RES
<222> LOCATION: (10)..(10)
<223> OTHER INFORMATION: Val or Leu
<220> FEATURE:
<223> OTHER INFORMATION: see specification as filed for detailed
      description of substitutions and preferred embodiments

<400> SEQUENCE: 8

Arg Ala Ser Gln Xaa Xaa Xaa Thr Xaa Xaa Ala
1               5                   10

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Phe or Thr
<220> FEATURE:
<221> NAME/KEY: MOD_RES
<222> LOCATION: (6)..(6)
<223> OTHER INFORMATION: Tyr or Ala
<220> FEATURE:
<223> OTHER INFORMATION: see specification as filed for detailed
      description of substitutions and preferred embodiments

<400> SEQUENCE: 9

Ser Ala Ser Xaa Leu Xaa Ser
1               5

<210> SEQ ID NO 10
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (3)..(3)
<223> OTHER INFORMATION: Tyr, Gly, Phe or Ser
<220> FEATURE:
<221> NAME/KEY: MOD_RES
<222> LOCATION: (4)..(4)
<223> OTHER INFORMATION: Leu, Tyr, Phe or Trp
<220> FEATURE:
<221> NAME/KEY: MOD_RES
<222> LOCATION: (5)..(5)
<223> OTHER INFORMATION: Tyr, Asn, Ala, Thr, Gly, Phe or Ile
<220> FEATURE:
<221> NAME/KEY: MOD_RES
<222> LOCATION: (6)..(6)
<223> OTHER INFORMATION: His, Val, Pro, Thr or Ile
<220> FEATURE:
<221> NAME/KEY: MOD_RES
<222> LOCATION: (8)..(8)
<223> OTHER INFORMATION: Ala, Trp, Arg, Pro or Thr
<220> FEATURE:
<223> OTHER INFORMATION: see specification as filed for detailed
      description of substitutions and preferred embodiments

<400> SEQUENCE: 10

Gln Gln Xaa Xaa Xaa Xaa Pro Xaa Thr
1               5

<210> SEQ ID NO 11
<211> LENGTH: 23
<212> TYPE: PRT
```

-continued

<213> ORGANISM: Homo sapiens

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 12
<211> LENGTH: 15
<212> TYPE: PRT
<213> ORGANISM: Homo sapiens

<400> SEQUENCE: 12

Trp Tyr Gln Gln Lys Pro Gly Lys Ala Pro Lys Leu Leu Ile Tyr
1               5                   10                  15

<210> SEQ ID NO 13
<211> LENGTH: 32
<212> TYPE: PRT
<213> ORGANISM: Homo sapiens

<400> SEQUENCE: 13

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 14
<211> LENGTH: 11
<212> TYPE: PRT
<213> ORGANISM: Homo sapiens

<400> SEQUENCE: 14

Phe Gly Gln Gly Thr Lys Val Glu Ile Lys Arg
1               5                   10

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Thr Phe Ser Asp Ser Trp Ile His
1               5                   10

<210> SEQ ID NO 16
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ala Trp Ile Ser Pro Tyr Gly Gly Ser Thr Tyr Tyr Ala Asp Ser Val
1               5                   10                  15

Lys Gly

<210> SEQ ID NO 17
<211> LENGTH: 11

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Arg Ala Ser Gln Asp Val Ser Thr Ala Val Ala
1               5                   10

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Ser Ala Ser Phe Leu Tyr Ser
1               5

<210> SEQ ID NO 19
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gln Gln Tyr Leu Tyr His Pro Ala Thr
1               5

<210> SEQ ID NO 20
<211> LENGTH: 118
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ala
        115

<210> SEQ ID NO 21
<211> LENGTH: 108
<212> TYPE: PRT
<213> ORGANISM: Artificial Sequence
```

```
<220> FEATURE:
<223> OTHER INFORMATION: Description of Artificial Sequence: Synthetic
      polypeptide

<400> SEQUENCE: 21

Asp Ile Gln Met Thr Gln Ser Pro Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg
            100                 105

<210> SEQ ID NO 22
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 22

Glu Val Gln Leu Val Glu Ser Gly Gly Gly Leu Val Gln Pro Gly Gly
1               5                   10                  15

Ser Leu Arg Leu Ser Cys Ala Ala Ser Gly Tyr Thr Phe Thr Asn Tyr
            20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
    50                  55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                85                  90                  95

Ala Lys Tyr Pro His Tyr Tyr Gly Ser Ser His Trp Tyr Phe Asp Val
            100                 105                 110

Trp Gly Gln Gly Thr Leu Val Thr Val Ser Ser
        115                 120

<210> SEQ ID NO 23
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Asp Ile Gln Met Thr Gln Ser Pro Ser Leu Ser Ala Ser Val Gly
1               5                   10                  15

Asp Arg Val Thr Ile Thr Cys Ser Ala Ser Gln Asp Ile Ser Asn Tyr
            20                  25                  30
```

```
Leu Asn Trp Tyr Gln Gln Lys Pro Gly Lys Ala Pro Lys Val Leu Ile
            35                  40                  45

Tyr Phe Thr Ser Ser Leu His Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Ser Thr Val Pro Trp
                 85                  90                  95

Thr Phe Gly Gln Gly Thr Lys Val Glu Ile Lys Arg
            100                 105
```

<210> SEQ ID NO 24
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 24

```
Gly Tyr Thr Phe Thr Asn Tyr Gly Met Asn
 1               5                  10
```

<210> SEQ ID NO 25
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

```
Trp Ile Asn Thr Tyr Thr Gly Glu Pro Thr Tyr Ala Ala Asp Phe Lys
 1               5                  10                  15

Arg
```

<210> SEQ ID NO 26
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

```
Tyr Pro His Tyr Tyr Gly Ser Ser His Trp Tyr Phe Asp Val
 1               5                  10
```

<210> SEQ ID NO 27
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 27

```
Ser Ala Ser Gln Asp Ile Ser Asn Tyr Leu Asn
 1               5                  10
```

<210> SEQ ID NO 28
<211> LENGTH: 7
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 28

Phe Thr Ser Ser Leu His Ser
1               5

<210> SEQ ID NO 29
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gln Gln Tyr Ser Thr Val Pro Trp Thr
1               5

<210> SEQ ID NO 30
<211> LENGTH: 25
<212> TYPE: PRT
<213> ORGANISM: Homo sapiens

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser
            20                  25

<210> SEQ ID NO 31
<211> LENGTH: 13
<212> TYPE: PRT
<213> ORGANISM: Homo sapiens

<400> SEQUENCE: 31

Trp Val Arg Gln Ala Pro Gly Lys Gly Leu Glu Trp Val
1               5                   10

<210> SEQ ID NO 32
<211> LENGTH: 32
<212> TYPE: PRT
<213> ORGANISM: Homo sapiens

<400> SEQUENCE: 32

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 33
<211> LENGTH: 11
<212> TYPE: PRT
<213> ORGANISM: Homo sapiens

<400> SEQUENCE: 33

Trp Gly Gln Gly Thr Leu Val Thr Val Ser Ala
1               5                   10

<210> SEQ ID NO 34
<211> LENGTH: 23
<212> TYPE: PRT
<213> ORGANISM: Homo sapiens

<400> SEQUENCE: 34

```
Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 35
<211> LENGTH: 15
<212> TYPE: PRT
<213> ORGANISM: Homo sapiens

<400> SEQUENCE: 35

Trp Tyr Gln Gln Lys Pro Gly Lys Ala Pro Lys Leu Leu Ile Tyr
1               5                   10                  15

<210> SEQ ID NO 36
<211> LENGTH: 32
<212> TYPE: PRT
<213> ORGANISM: Homo sapiens

<400> SEQUENCE: 36

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 37
<211> LENGTH: 11
<212> TYPE: PRT
<213> ORGANISM: Homo sapiens

<400> SEQUENCE: 37

Phe Gly Gln Gly Thr Lys Val Glu Ile Lys Arg
1               5                   10
```